United States Patent [19]
Dryden et al.

[11] Patent Number: 6,112,161
[45] Date of Patent: Aug. 29, 2000

[54] METHOD, APPARATUS, AND ARTICLE OF MANUFACTURE FOR ENHANCED INTERGRATION OF SIGNALS

[75] Inventors: Paul C. Dryden, West Chester; Bruce D. Quimby, Lincoln University, both of Pa.

[73] Assignee: Hewlett-Packard, Palo Alto, Calif.

[21] Appl. No.: 08/932,150

[22] Filed: Sep. 17, 1997

[51] Int. Cl.[7] .................................................. G01N 30/86
[52] U.S. Cl. .............................. 702/85; 702/66; 702/111; 702/191; 702/193; 73/23.23
[58] Field of Search ................................... 702/85, 32, 22, 702/30, 31, 66, 71, 73, 74, 86, 104, 107, 111, 116, 124, 126, 183, 189–191, 193, 195, 197, FOR 164–FOR 166, FOR 110, 75, 106, FOR 107, 70, 69; 73/23.23, 23.21, 23.22, 23.35, 23.36, 61.57, 1.02, 1.03, 1.06, 1.07, 1.59, 1.61, 1.88; 364/528.01; 395/500.27, 500.33, 500.32, 500.3; 324/620, 613, 76.17

[56] References Cited

U.S. PATENT DOCUMENTS

| | | | |
|---|---|---|---|
| 3,555,260 | 1/1971 | Karohl | 73/23.23 |
| 4,170,893 | 10/1979 | Kleiss | 73/23.23 |
| 4,802,102 | 1/1989 | Lacey | 73/23.23 |
| 4,837,726 | 6/1989 | Hunkapiller | 702/32 |
| 4,941,101 | 7/1990 | Crilly | 702/32 |
| 5,592,402 | 1/1997 | Beebe et al. | 395/500.27 |

*Primary Examiner*—Hal Wachsman
*Attorney, Agent, or Firm*—Robert C. Sismilich

[57] ABSTRACT

A method, apparatus, and article of manufacture for enhanced integration of signals, such as those generated by chromatographs. In one embodiment an approximate baseline used for integration of a signal is improved to reduce error. Alternate embodiments filter drift, noise, or both from a signal prior to integration or simulated distillation. The signals are processed according to a computer program stored in a memory. The methods include steps for subtracting an approximate baseline from the signal, defining a noise band in the resulting difference, and forming a composite baseline by substituting signal data for baseline data wherever the difference does not exceed the threshold, thus leaving the parts of the approximate baseline that correspond to signal peaks unchanged.

21 Claims, 18 Drawing Sheets

METHOD, APPARATUS, AND ARTICLE OF MANUFACTURE FOR ENHANCED INTERGRATION OF SIGNALS

FIELD OF THE INVENTION

The present invention relates generally to two-dimensional signal analysis, and more particularly to a method, apparatus, and article of manufacture for the integration of time-varying signals which consist of one or more peaks rising above a background level containing noise and drift, such as those generated by chromatographic systems.

BACKGROUND OF THE INVENTION

A typical chromatographic analysis system includes an injection port into which the sample is injected and mixed with an inert gas or liquid, a column through which the various dissolved components of the sample will travel at a rate related to the characteristics of the specific components, and a detector for measuring the concentration of each component as it exits the column and generating a time-varying signal corresponding to its concentration. The time between the injection of a sample and the detection of a specific component is called the retention time of that component. The time-varying signal is sent to a computing apparatus that integrates the signal by executing a computer program. The computing apparatus often provides a two-dimensional visual display of the signal, known in the art as a chromatogram. The x-axis of the chromatogram represents time, and the y-axis typically corresponds to the amplitude of the signal.

A typical time-varying signal 101 generated by a gas chromatograph is shown in FIG. 1. Peaks 102 in the signal correspond to the detection by the chromatograph of specific components of the chemical sample. The height of the peak above the background level 103 of the signal, and the amount of area under the peak and above the background level, correlate to the amount of the respective component present in the sample. This information can be used for many applications, such as to check for the presence of, or to ensure the absence of, particular components in the sample, or to verify the proper concentration of the component in the sample.

The computer program includes an integration method which detects peaks, determines the retention time 104 at which they occur, and determines their heights and areas. To determine peak height and peak area, the computer must first determine a baseline for each peak. The baseline is a reference level that corresponds to the background level of the signal when no peaks are present. The background level is typically a non-zero signal that may include noise (higher in frequency than the peaks) and drift (lower in frequency than the peaks; also known as wander).

A chromatographer visually drawing the baseline under a particular peak would extrapolate it through the center of the noise on both sides of the peak with a slope corresponding to the drift. However, the presence of noise and drift in the background level make determining an accurate baseline difficult for a computer. As a result, prior art integration methods, in the presence of noise and drift, typically do not produce the same baseline as would a chromatographer looking at the signal visually.

A first prior art integration method sets the baseline by looking at only a small region of the signal at a time. As shown in FIG. 2, this method sets the baseline 201 too low where noise 202 is present because the method finds the lowest points near both sides of the peak and draws the baseline 201 between these points. If, as shown in FIG. 3, the detector produces a negative background signal disturbance 302 in the presence of two large peaks close together, this integration method will use the lowest point of the disturbance to set the baseline 301. Also, since the threshold level for signal detection has to be set conservatively in order to avoid misidentifying background noise as peaks, some valid peaks may not be detected. This problem worsens as the signal-to-noise ratio decreases, as shown by the absence of any identified peaks for the signal 401 of FIG. 4.

A second prior art method extends the baseline back in time from the average background level that occurs towards the end of an analysis in order to compensate for the effects of venting the solvent peak. As shown in FIG. 5, this method sets the baseline 501 too low in the region where background drift 504 occurs after the venting of the solvent peak 502. In addition, if the background continues to drift throughout the run, this method may misinterpret a hump in the drift as a false peak 505.

A third prior art method establishes a baseline using curve fitting techniques. However, the complexity of curve fitting increases with the complexity of the baseline shape, which makes such a method difficult to implement and requires excessive computational power when the signal contains noise and drift. To reduce complexity, this method may alternatively divide the baseline into multiple segments to allow simpler, piecewise curve fitting. However, this modification introduces discontinuities between curve segments that affect the accuracy of integration results.

A fourth prior art method filters noise by performing a fourier transform. However, it is difficult to filter out all the noise without distorting the peaks, since typically there is overlap in frequency content between the peaks and the noise.

A chromatogram which displays an accurate baseline along with the signal is readily usable by an expert chromatographer. However, chromatograms are sometimes analyzed by nonchromatographers, for whom baseline drift and noise can cause confusion. A better display for non-experts would present a chromatogram from which the baseline noise and drift have been filtered, leaving only undistorted peaks and a flattened baseline. A filtered chromatogram could be accurately integrated using simple integration methods, and would provide more accurate results when analyzed using simulated distillation techniques.

In the analysis of signals consisting of one or more peaks rising above a background level which contains noise, drift, or a combination of both, there has been a need for a simple method of determining an accurate baseline which eliminates noise and drift without distorting the peaks, in order to calculate accurate peak heights and areas. There has also been a corresponding need for filtering the signal to eliminate noise, drift, or both, prior to display, integration, or simulated distillation.

SUMMARY OF THE INVENTION

The present invention may be implemented as a method of optimizing the baseline of a signal to account for noise and drift without introducing peak distortion. This method facilitates accurate measurements of peak height and peak area during integration, without undue complexity. The present invention may alternatively be implemented as a simple method of filtering the signal to attenuate noise, drift, or both. A chomatogram filtered according to this invention communicates information more clearly to non-chromatographers, can be accurately integrated by simple integration methods, and provides accurate results in simulated distillation analysis. The invention may be embodied in a program storage medium readable by a computer which contains program code that performs the baseline optimization and signal filtering methods. It may also be embodied in a computing apparatus having a computer program which performs the baseline optimization and signal filtering methods; a gas chromatographic apparatus may optionally be interfaced to the computing apparatus.

A preferred first embodiment of the present invention is a method that produces an improved baseline from an approximate baseline by subtracting the approximate baseline from the signal, defining a noise band in the resulting difference, forming a composite baseline by substituting signal data for approximate baseline data at those segments of the baseline where the difference falls within the noise band (thus leaving the segments of the approximate baseline that correspond to the signal peaks unchanged), and smoothing the composite baseline to form the improved baseline. These steps may optionally be performed repetitively to further improve the baseline, using the improved baseline from the prior iteration as the approximate baseline for the subsequent iteration. A further option is to integrate the signal using the improved baseline to obtain the peak height and peak area.

A preferred second embodiment of the present invention is a method that filters a signal to attenuate drift by smoothing the signal to form an approximate baseline, subtracting the approximate baseline from the signal, defining a noise band in the resulting difference, forming a composite baseline by substituting signal data for approximate baseline data at those segments of the baseline where the difference falls within the noise band (thus leaving the segments of the approximate baseline that correspond to the signal peaks unchanged), smoothing the composite baseline, and subtracting the smoothed composite baseline from the initial signal to form the filtered signal with drift attenuated. These steps may optionally be performed repetitively to further filter the drift, using the smoothed composite baseline from the prior iteration as the approximate baseline for the subsequent iteration. A further option is to integrate the filtered signal to obtain the peak height and peak area once the baseline has been improved using a simple integration algorithm.

A preferred third embodiment of the present invention is a method that filters a signal to attenuate both noise and drift by smoothing the signal to form an approximate baseline, subtracting the approximate baseline from the signal, defining a noise band in the resulting difference, forming a composite baseline by substituting signal data for approximate baseline data at those segments of the baseline where the difference falls within the noise band (thus leaving the parts of the baseline that correspond to the signal peaks unchanged), and subtracting the composite baseline from the initial signal to form the filtered signal with noise and drift attenuated. These steps may optionally be performed repetitively to further filter the noise and drift, by smoothing the composite baseline from the prior iteration and then using it as the approximate baseline for the subsequent iteration. A further option is to integrate the filtered signal to obtain the peak height and peak area once the baseline has been improved using a simple integration algorithm. Alternatively, a simulated distillation analysis may be performed on the filtered signal.

A preferred fourth embodiment of the present invention is a method that filters a signal to attenuate noise by smoothing the signal to form an approximate baseline, subtracting the approximate baseline from the signal, defining a noise band in the resulting difference, forming an unsmoothed composite baseline by substituting signal data for approximate baseline data at those segments of the baseline where the difference falls within the noise band (thus leaving the parts of the baseline that correspond to the signal peaks unchanged), smoothing the composite baseline to form a smoothed composite baseline, and subtracting the unsmoothed composite baseline from the initial signal while adding the smoothed composite baseline to the initial signal to form the filtered signal with noise attenuated. These steps may optionally be performed repetitively to further filter the noise, using the smoothed composite baseline from the prior iteration as the approximate baseline for the subsequent iteration.

Other aspects and advantages of the present invention will become apparent from the following detailed description, taken in conjunction with the accompanying drawings, illustrating by way of example the principles of the invention. The claims alone, not the preceding summary or the following detailed description, define the invention.

DESCRIPTION OF THE PREFERRED EMBODIMENT

Figure 1:
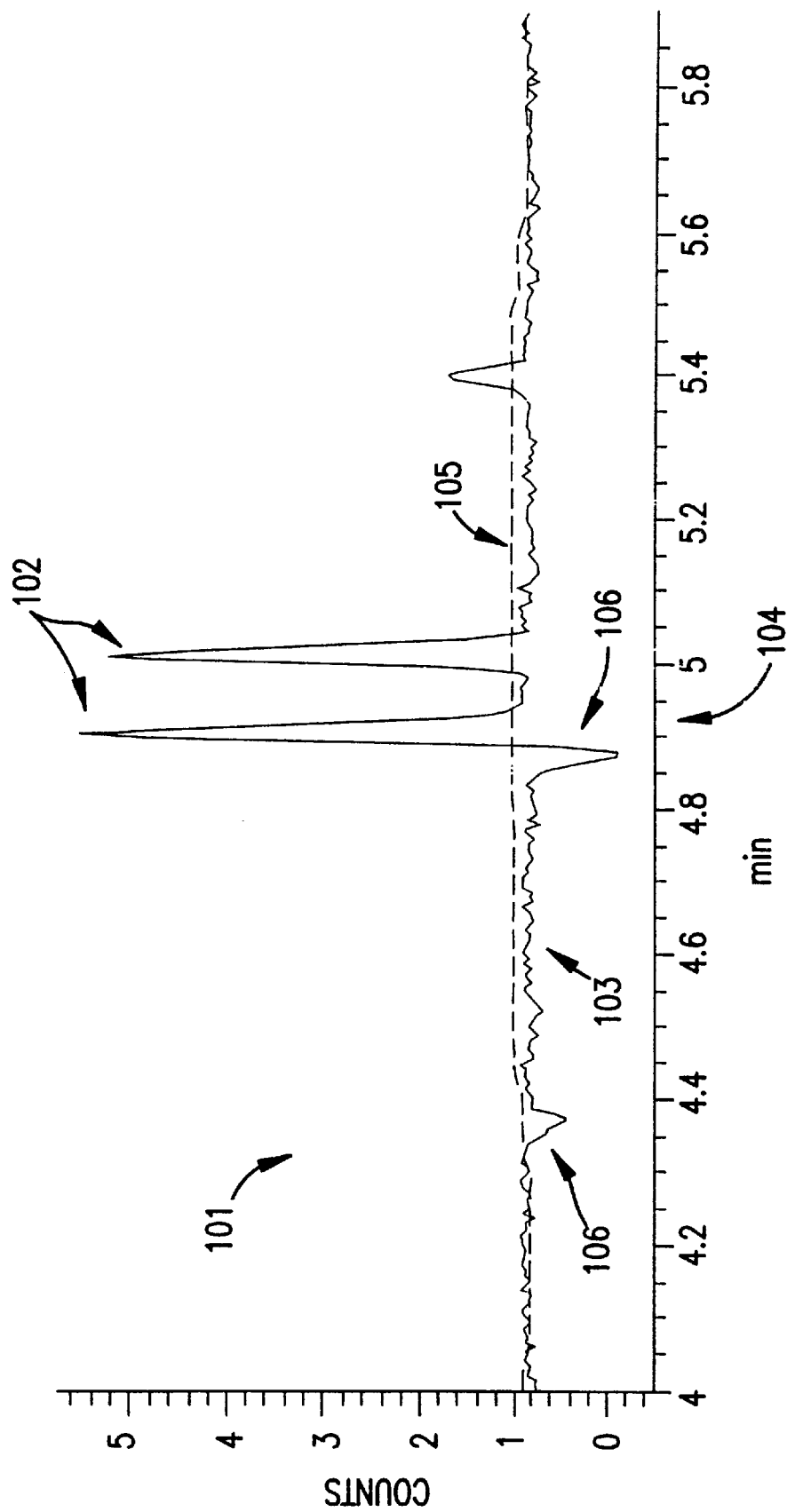
FIG. 1 is an exemplary chromatogram showing a chromatographic signal including peaks and noise, and an approximate baseline.
Figure 2:
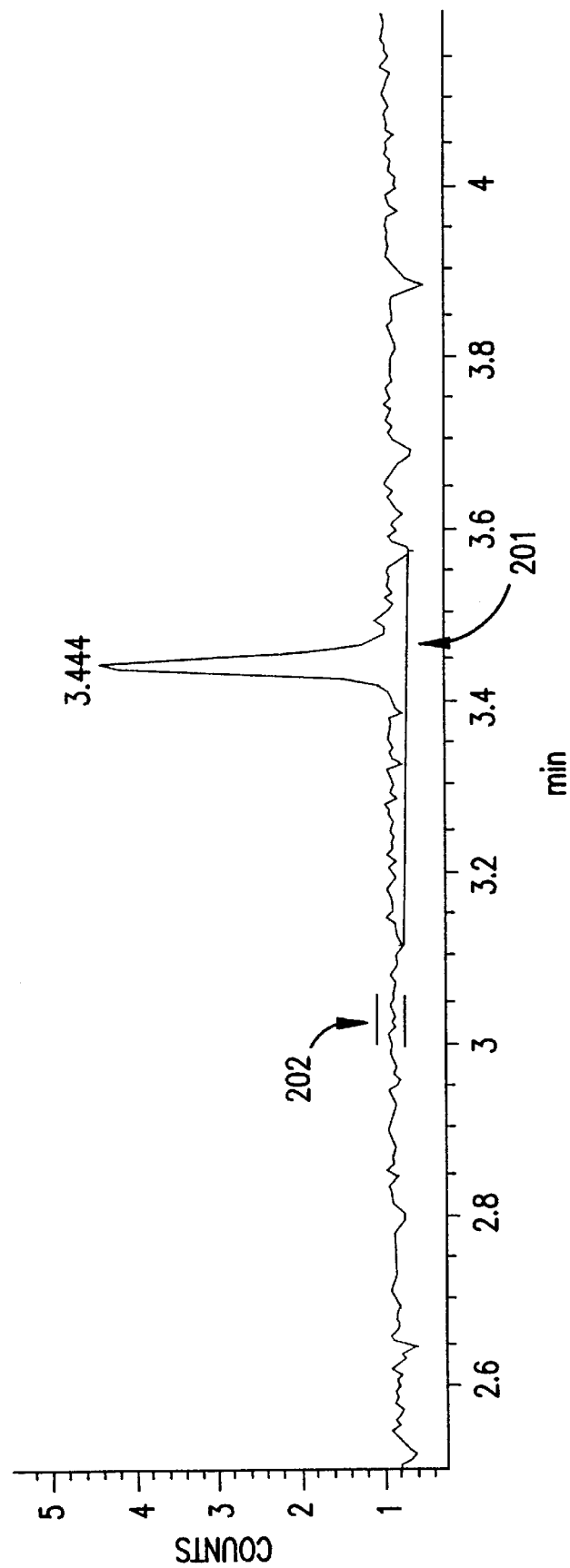
FIG. 2 is an exemplary chromatogram showing a chromatographic signal having background noise and an inaccurate baseline resulting from use of a prior art integration method.
Figure 3:
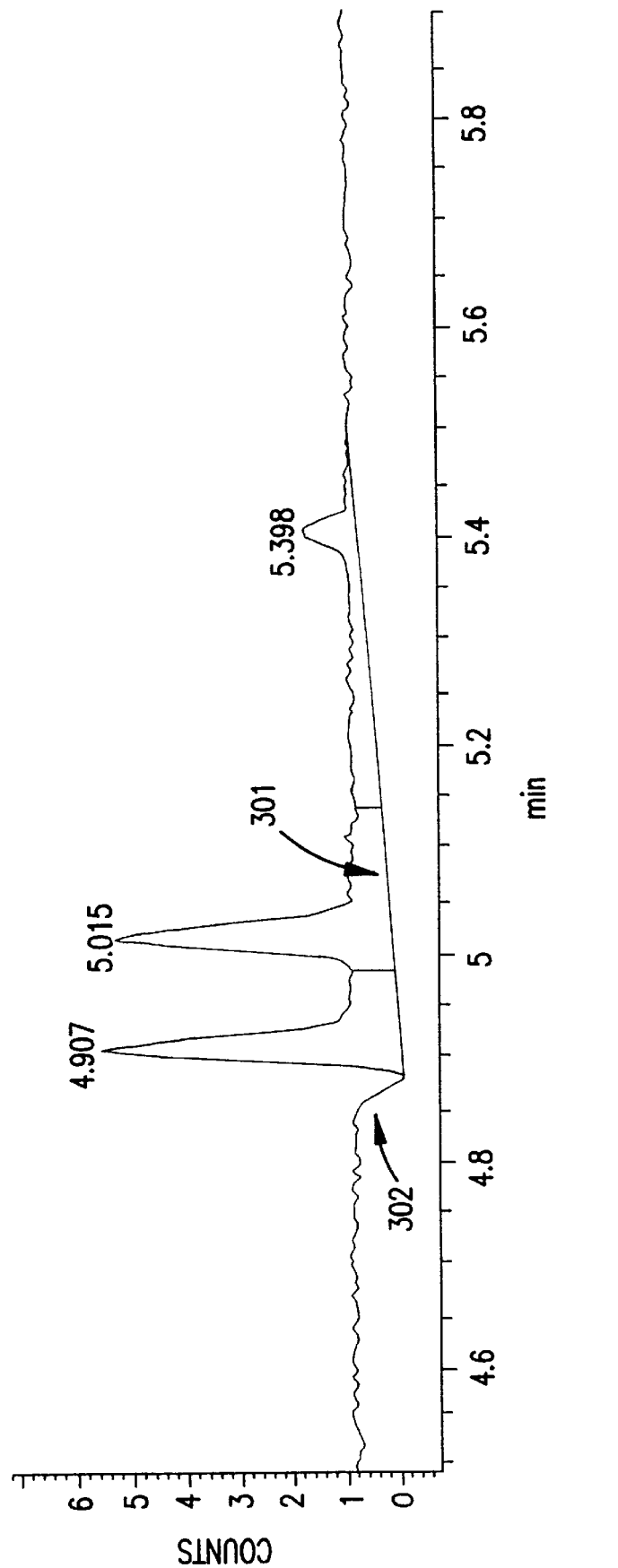
FIG. 3 is an exemplary chromatogram showing a chromatographic signal having a negative background disturbance and an inaccurate baseline resulting from use of a prior art integration method.
Figure 4:
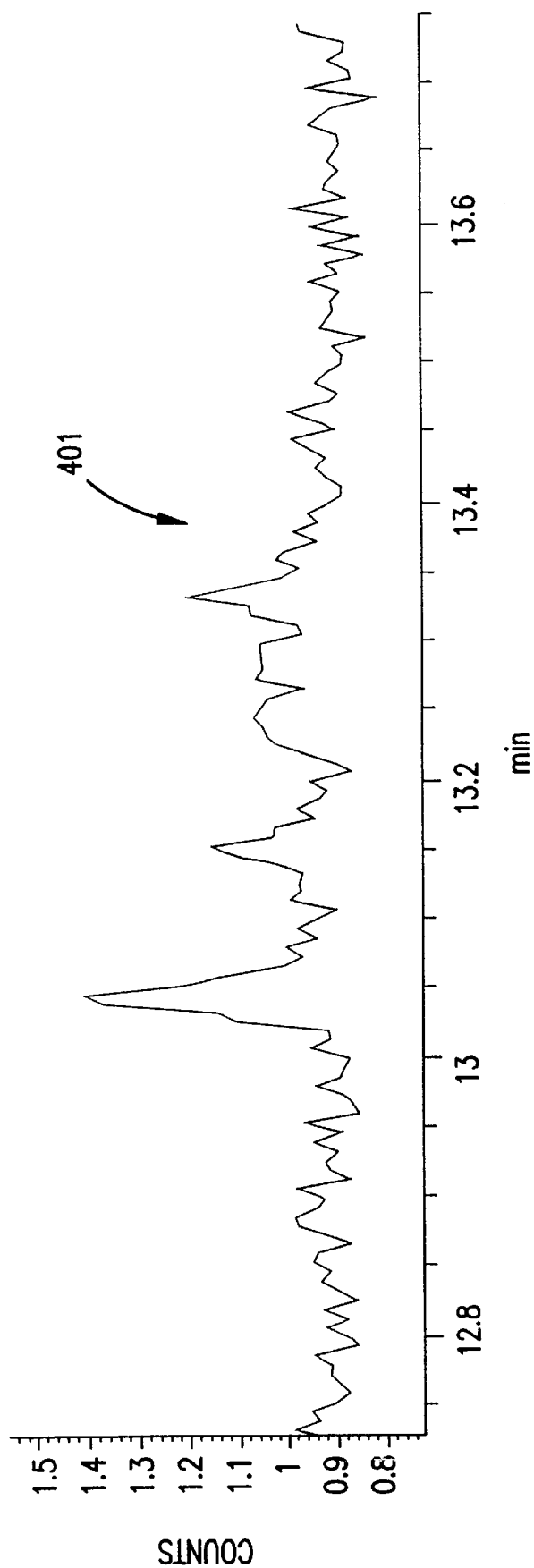
FIG. 4 is an exemplary chromatogram showing a chromatographic signal with a low signal-to-noise ratio where no peaks are detected by a prior art integration method.

As shown in the drawings for purposes of illustration and as described in the following detailed description, the method, apparatus, and article of manufacture of the present invention improve the analysis of electronic signals consisting of one or more peaks greater in amplitude than a background level containing noise higher in frequency than the peaks, drift lower in frequency that the peaks, or both noise and drift. According to the present invention, integration and simulated distillation of these signals produce more accurate measurements, and the chromatograms of the analyzed signals can be understood more readily by non-experts. Prior methods of analyzing these signals have been unduly complex or have yielded less accurate measurements.

Electronic signals usable with the present invention can be generated by a variety of instrumentation, and may represent a variety of physical, electrical, or chemical properties. Examples of such instrumentation include, but are not limited to, gas and liquid chromatographs, spectrum analyzers, oscilloscopes, and seismographs. Signals from some instruments may be generally bipolar, having sinusoidally-shaped peaks centered around the background level. The signals from chromatographs are generally unipolar, having Gaussian-shaped peaks rising above the background level (however, signals dropping below the background level, often called negative background disturbances, may occur as well). A gas chromatograph generates the signals according to the preferred practice of the invention, and therefore the detailed description of the invention will be directed to a gas chromatographic analytical system. However, it should be understood that the teachings herein are applicable to any electronic signals having the amplitude and frequency properties described above.

Gas chromatographs usable in the practice of the present invention include the Hewlett-Packard 6890 series and 5890 series, while liquid chromatographs include the Hewlett-Packard 1100 series and 1050 series.

System, Apparatus, and Program Storage Medium

Figure 6:
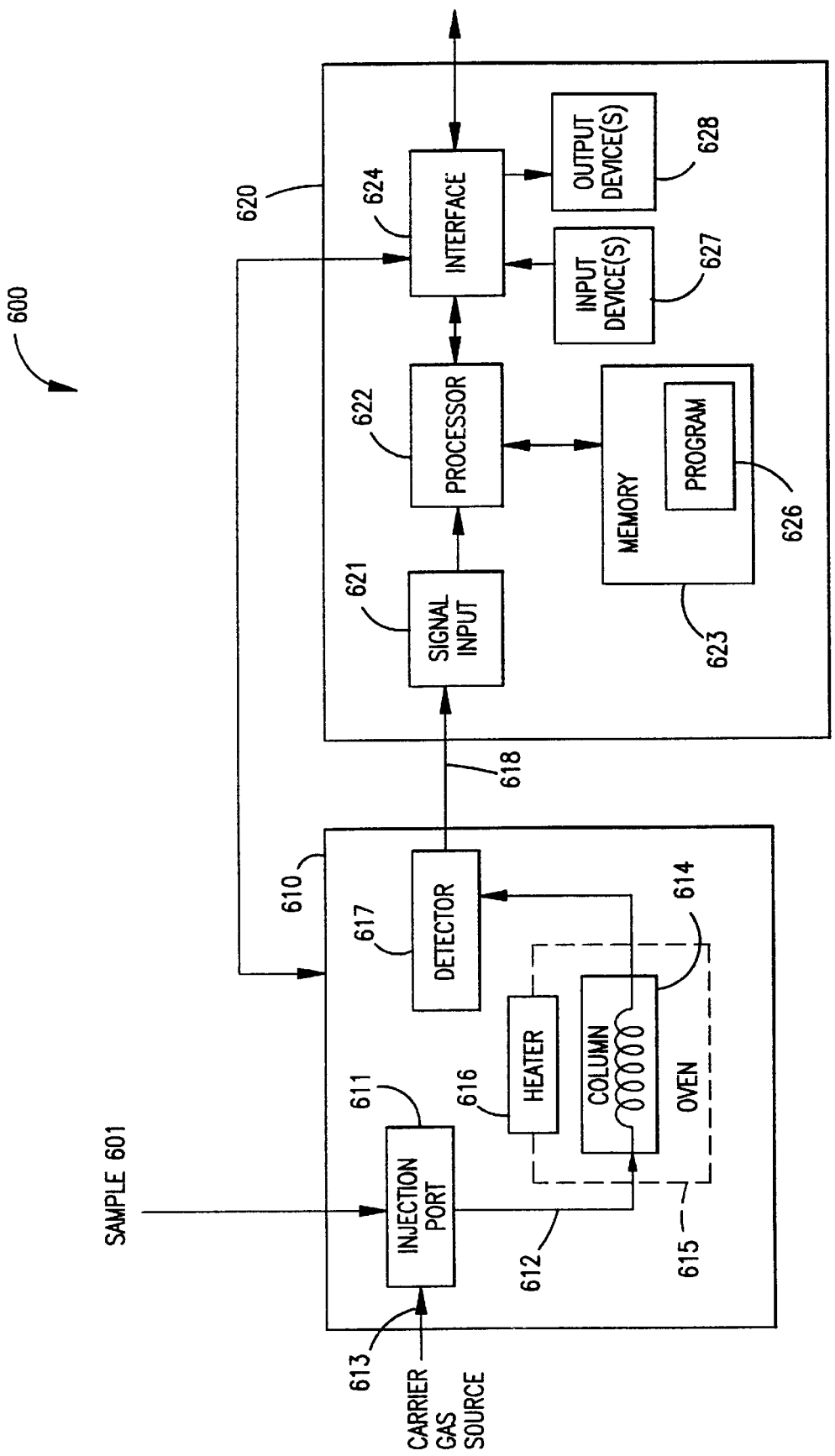
FIG. 6 is a block diagram of a gas chromatographic instrumentation system suitable for the practice of the present invention.

The preferred embodiment of an analytical instrument system 600 illustrated in FIG. 6 includes a gas chromatograph 610, and a computer system 620 having a signal input 621, processor 622, memory 623, interface 624, input device 627, and output device 628. In order to perform a chromatographic separation of a sample 601, a quantity of the sample 601 is injected into a fluid stream, preferably in the form of a pressurized carrier gas, via an injection port 611 supplied with carrier gas stream 613. The injection port 611 provides a portion of the sample/carrier gas mixture 612 to a separation column 614. The column 614 is positioned within a temperature-controlled thermal chamber or oven 615. The carrier gas/sample combination 612 passing through the column 614 is exposed to a temperature profile resulting from the operation of the heater 616 within the oven 614.

As the carrier gas (containing the separated components of the sample) exits the column 614, the presence of one or more of the constituent components of the sample is detected by a detector 617. The detector 617 can be any of the GC detectors known in the art, as long as it is capable of determining at least one physicochemical property of the carrier gas which exits the column 614.

Such GC detectors include the flame ionization detector (FID), photoionization detector (PID), nitrogen phosphorous detector (NPD), flame photometric detector (FPD), thermal conductivity detector (TCD), atomic emission detector (AED), electrolytic conductivity detector (ELCD), and electron capture detector (ECD). Mass spectral detectors and infrared spectral detectors are also known.

The detector output signal 618 may be either in analog or digital electronic form. The detector output signal is then received by the signal input 621 for communication to the processor 622. If the signal is in analog form, the signal input may include an analog-to-digital converter (not shown) to convert the signal to a computer-readable form. The converted detector output signal is typically stored in the memory 623. Preferably, the detector output signal is provided in the form of data representative of one or more peaks each corresponding to detection of a constituent component of the sample, the peak(s) rising above a background signal level containing noise, drift, or both noise and drift. The operations performed by the computer system 620 on the signal data in accordance with the present invention will be described subsequently.

The processor 622 may include computing devices amenable to the practice of this invention, e.g., one or more computing devices such as computers, microprocessors, microcontrollers, switches, logic gates, or any equivalent logic device capable of performing the computations described herein below. The processor 622 preferably is coupled with the interface 624, input device 627, and output device 628. Input devices preferably include one or more of a keyboard, keypad, pointing device, or remote computer (not shown) for inputting operating condition parameters, system calibration data, and the like. Output devices preferably include alphanumeric or video displays, printers, or a remote computer (not shown).

The preferred computer system 620 further includes memory 623 in the form of volatile and non-volatile devices in which computer programs 626, input and output information, operating condition parameters, and system information can be stored and retrieved. Contemplated computer programs 626 include method embodiments of the present invention. Contemplated memory devices include, but are not limited to, ROM, RAM, floppy disk, hard disk, and CD-ROM. Operating commands, detector response attributes, column temperature programs, and other information necessary to perform a chromatographic analysis may be entered into the processor 622 by way of an input device 627 or retrieved from memory 623.

The chromatogram, peak heights, and peak areas calculated by the processor 622 for the signal may be transmitted to an output device 628 and displayed or printed. The interface 624 may further comprise network and bus system (input/output or I/O) controllers, isolation devices, clocks, and other related electronic components for performing control, processing, and communication tasks other than those described herein. A remote computing apparatus (not shown) may connect to the interface 624 and cooperate with the computer system 620 to implement the present invention as a client/server application.

The method embodiments of the present invention are operable in the system 600, and may be contained in the memory 623.

Signal Data Representation and Storage

The signal data, herein referred to mathematically as s(x), is stored in the memory 623 in a format usable for two-dimensional data. The dependent variable s(x) represents the signal in a chromatogram, and the independent variable x represents time. In a first embodiment where the values of x represent a fixed interval of time, s(x) may be stored in a data structure comprising a one-dimensional array of signal data points. In a second embodiment where the values of x represent a variable interval of time, a data structure comprising an array of ordered pairs (x,s(x)) may be used. Data structures of the corresponding type may be used to contain the other dependent variable data disclosed in the remainder of the detailed description, such as baselines b(x) and baseline-adjusted signals a(x).

Smoothing Algorithm

Several embodiments of the present invention include a method step for smoothing a signal or a baseline. The purpose of this step is to attenuate high frequencies (noise and peaks) in the signal or baseline while having little or no effect on low frequencies (drift). Smoothing conserves area; when a peak gets smoothed, its area gets redistributed over a wider range. Visually, the peak becomes lower in amplitude but extends over a wider period of time.

A variety of high-frequency filtering algorithms may be utilized to perform the smoothing step. The general approach to smoothing is to replace each of the original data points with the weighted average of it and its nearest neighbors. The number of points averaged, and the weighting factors applied to each point, determine the frequency-response curve. There is one complication to any smoothing algorithm: data points near the start and end of the data do not have the required number of nearest neighbors on one side, so their smoothed values cannot be calculated in the usual way. Often the solution to this problem is to have fewer points in the smoothed data than were in the original data. The first and last (n−1)/2 points (where n is the number of points averaged) are simply missing. Where multi-pass smoothing is applied, more data will being lost at each subsequent pass.

The preferred smoothing algorithm uses a simple "boxcar" filter in which all of the weighting factors are the same and the only variable is the number of points averaged. To mitigate the data distortion caused by boxcar filtering, a second pass is performed with fewer points averaged. This achieves high-frequency rejection with less distortion, and is functionally equivalent to smoothing with unequal weighting factors. To avoid data loss at the start and end of the signal or baseline, the algorithm extrapolates additional data points prior to smoothing which are included in the filtering.

Figure 7:
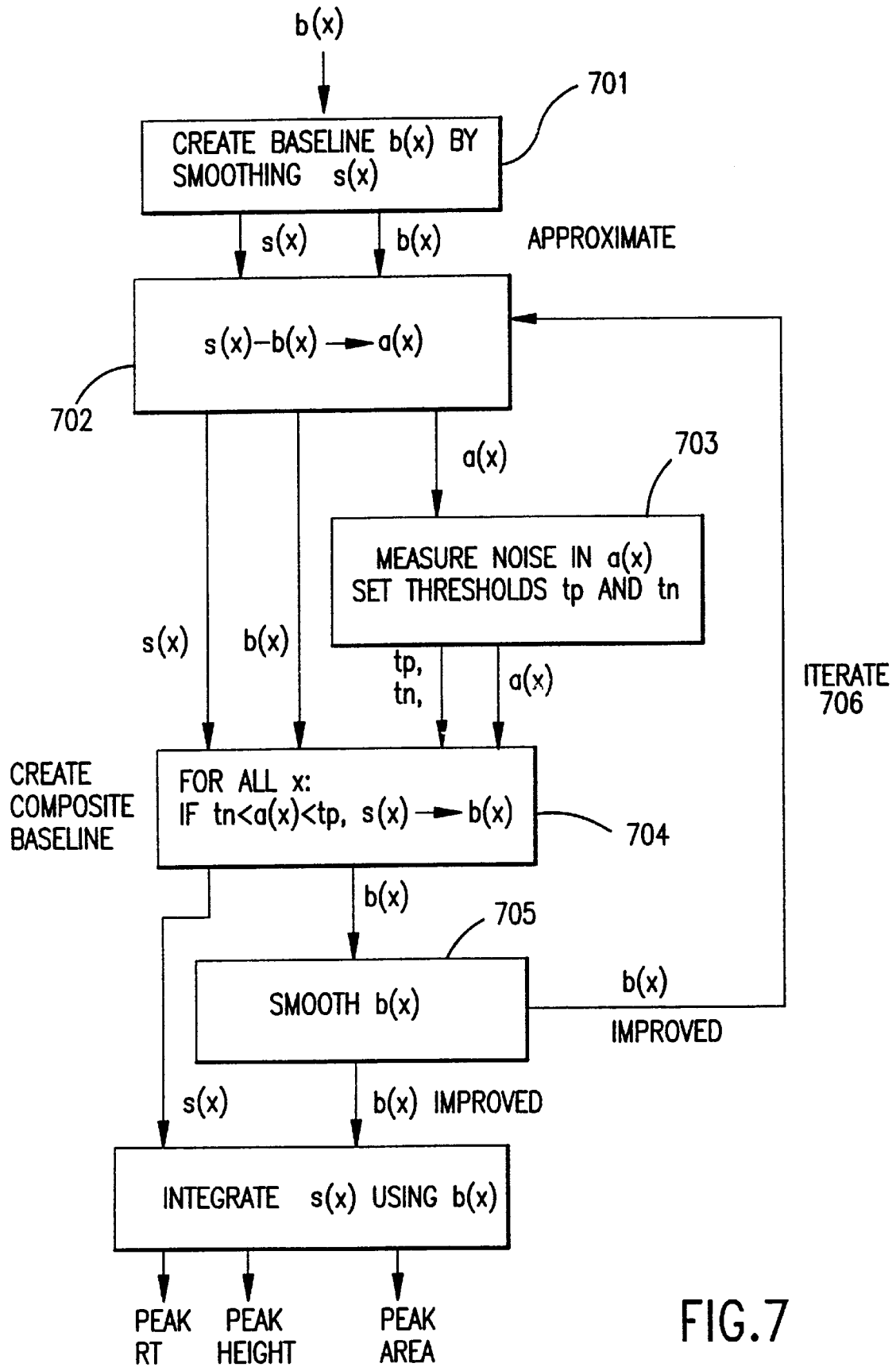
FIG. 7 is a simplified representation of an algorithm for performing baseline optimization in accordance with the present invention.

An alternate smoothing embodiment having unequal weighting factors uses a Savitzky-Golay (least-squares) filter. The variables in least-squares smoothing are the number of points averaged and the order of equation to which the data is to be fit. Although least-squares smoothing is more complex than boxcar smoothing, it can achieve a much better tradeoff between high-frequency attenuation and data distortion in a single pass. Data loss at the start and end of the signal or baseline can be avoided by using weighting factors that calculate the leastsquares value at a point other than the center point for each data point near the ends of the data.

Where an embodiment of the present invention calls for smoothing a signal that contains large, broad peaks to form an initial or approximate baseline, a more accurate initial baseline may be constructed after smoothing by forming a composite consisting of smoothed signal at those values of x where the signal approximately represents the background, and straight line segments between the endpoints of the smoothed signal to bridge the gaps where the signal approximately represents peaks. In order to determine where the signal represents peaks, the steps of forming a baseline-adjusted signal 702 and measuring the noise to set threshold values 703 may be performed, as shown in FIG. 7 and described subsequently.

Noise Measuring Algorithm

Several embodiments of the present invention include a method step for measuring the noise in a baseline-adjusted signal to define positive and negative threshold values, $t_P$ and $t_N$. The general approach to noise measurement involves dividing the signal up into smaller contiguous groups of data points and measuring the noise in each segment. In each segment, noise can be measured as either peak-to-peak or RMS noise. Peak-to-peak noise is the difference between the largest and the smallest values within the segment. RMS is the standard deviation of all of the data values within the group. Peak-to-peak is faster and easier to measure, but RMS is more accurate. Peak-to-peak noise is roughly six times larger than RMS noise for the same data. The preferred embodiment measures RMS noise. The thresholds $t_P$ and $t_N$ are set to plus and minus a factor times the RMS noise respectively. The preferred embodiment uses a factor of 2.0.

In measuring noise, the algorithm must ensure that it does not confuse peaks or drift with noise. In the preferred embodiment of noise measurement, any drift in the input signal has previously been subtracted from the baseline-adjusted signal in which the noise is measured. In order to exclude peaks, the preferred embodiment finds those segments with the smallest nonzero noise (background noise is assumed to be much lower than peaks). Once the noise measurements have been made for all segments, the smallest value can be chosen as the baseline noise. Since a particular detector may saturate above a certain signal level, causing it to have erroneously low noise, the preferred embodiment rejects any measured noise value of zero and selects the smallest non-zero value as the noise.

A further aspect of the noise measurement algorithm involves which groups of points are used to perform the measurement. The grouping can be as simple as dividing up the data points into some number of approximately equal groups (for example, one hundred groups of n/100 each, where n is the number of points in the signal) and calculating the noise of each group. A more sophisticated approach measures noise on more than 100 groups but still includes 1/100 of the data points in each group, for example the first group might be points 1 to 100, the second group points 51 to 150, etc. The preferred embodiment uses groups of data at one-data-point increments of the starting data point (for example, points 1 to 100, 2 to 101, 3 to 102, etc.).

Baseline Optimization Method

A preferred first embodiment of the present invention is a novel method of optimizing a baseline used for integration of a signal. The general approach is to begin with an initial approximate baseline that approximately tracks the background drift of the signal but has an error component, and improve the accuracy of this baseline by forming a composite baseline which tracks the signal noise and then smoothing the composite baseline to center the baseline within the noise. The error component of this improved baseline is smaller than that of the initial baseline.

As illustrated by applying the method of FIG. 7 to the signal data of FIG. 1 by way of example, the first embodiment begins with a initial step 701 in which an approximate baseline $b(x)$ 105 is generated. The approximate baseline may be generated by smoothing the signal $s(x)$, or by other methods which produce a baseline that generally tracks the background drift of the signal. The approximate baseline contains inaccuracies, particularly in the region of signal peaks and negative background disturbances, due to the area conservation of the smoothing algorithm.

Figure 8:
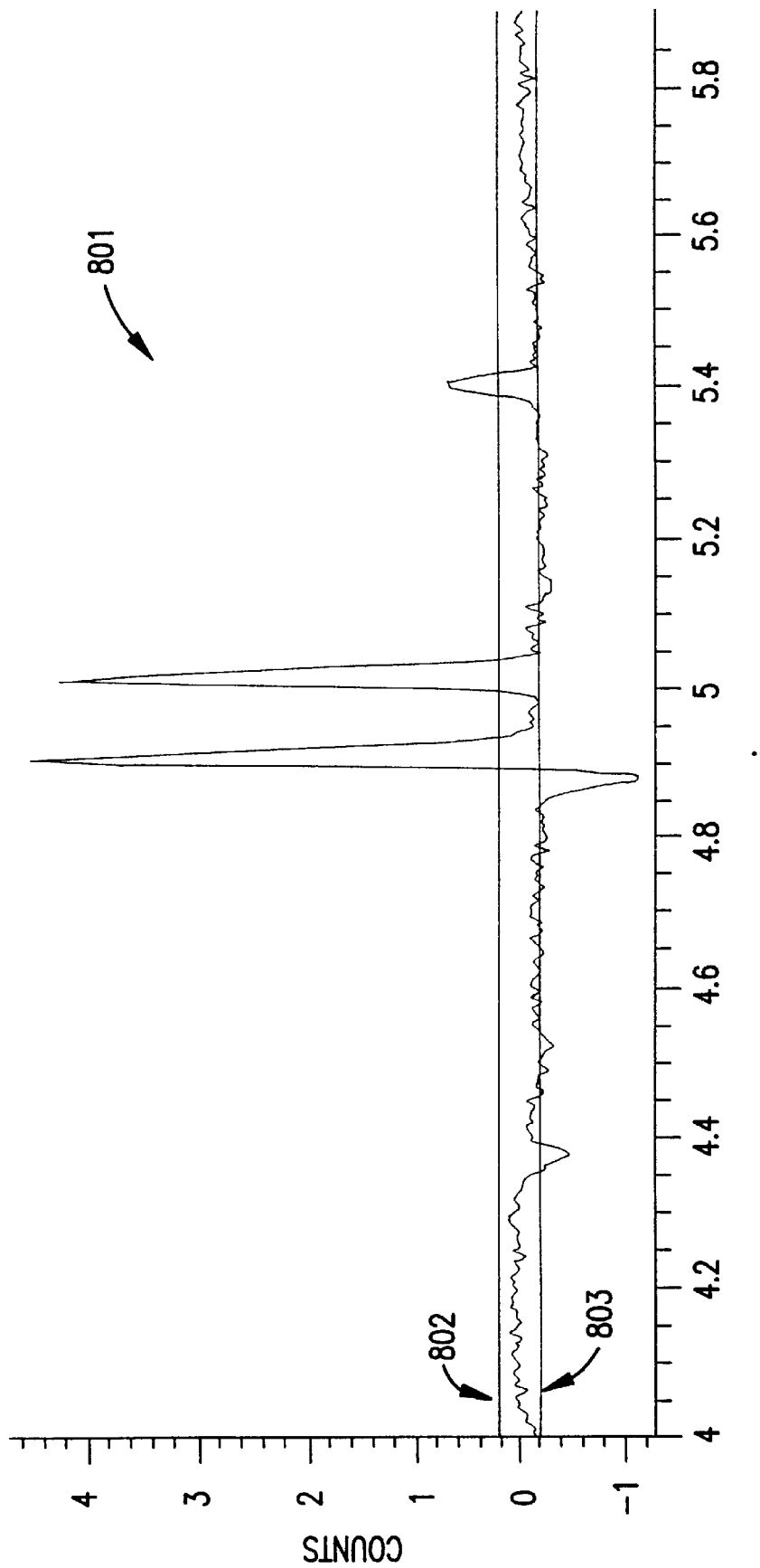
FIG. 8 is an exemplary chromatogram showing the baseline-adjusted signal generated by subtracting the approximate baseline from the signal of FIG. 1, and showing the threshold values defining the noise band for the signal.

Once the approximate baseline has been obtained, the following optimization steps can be performed one or more times to optimize the baseline. The first step 702 in optimization is to subtract the baseline from the signal, the difference forming a baseline-adjusted signal $a(x)$ 801 centered around zero counts, as shown in FIG. 8. The baseline-adjusted signal shows the deviation of the signal from the baseline; for example, at a value of x where the baseline $b(x)$ equals the signal $s(x)$, the baseline-adjusted signal $a(x)$ equals zero counts. Since the smoothed baseline from the prior step tracked the drift, drift will be attenuated in the baseline-adjusted signal.

The second optimizing step 703 is to calculate the noise in the baseline-adjusted signal $a(x)$ 801 and set positive $(t_P)$ 802 and negative $(t_N)$ 803 threshold values outside the range of, and surrounding, the noise. Signal data $s(x)$ at those values of x where the baseline-adjusted signal falls within the noise band defined by the thresholds approximately represent signal background. Signal data at those values of x where the baseline-adjusted signal falls outside this band approximately represent signal peaks or negative background disturbances.

Figure 9:
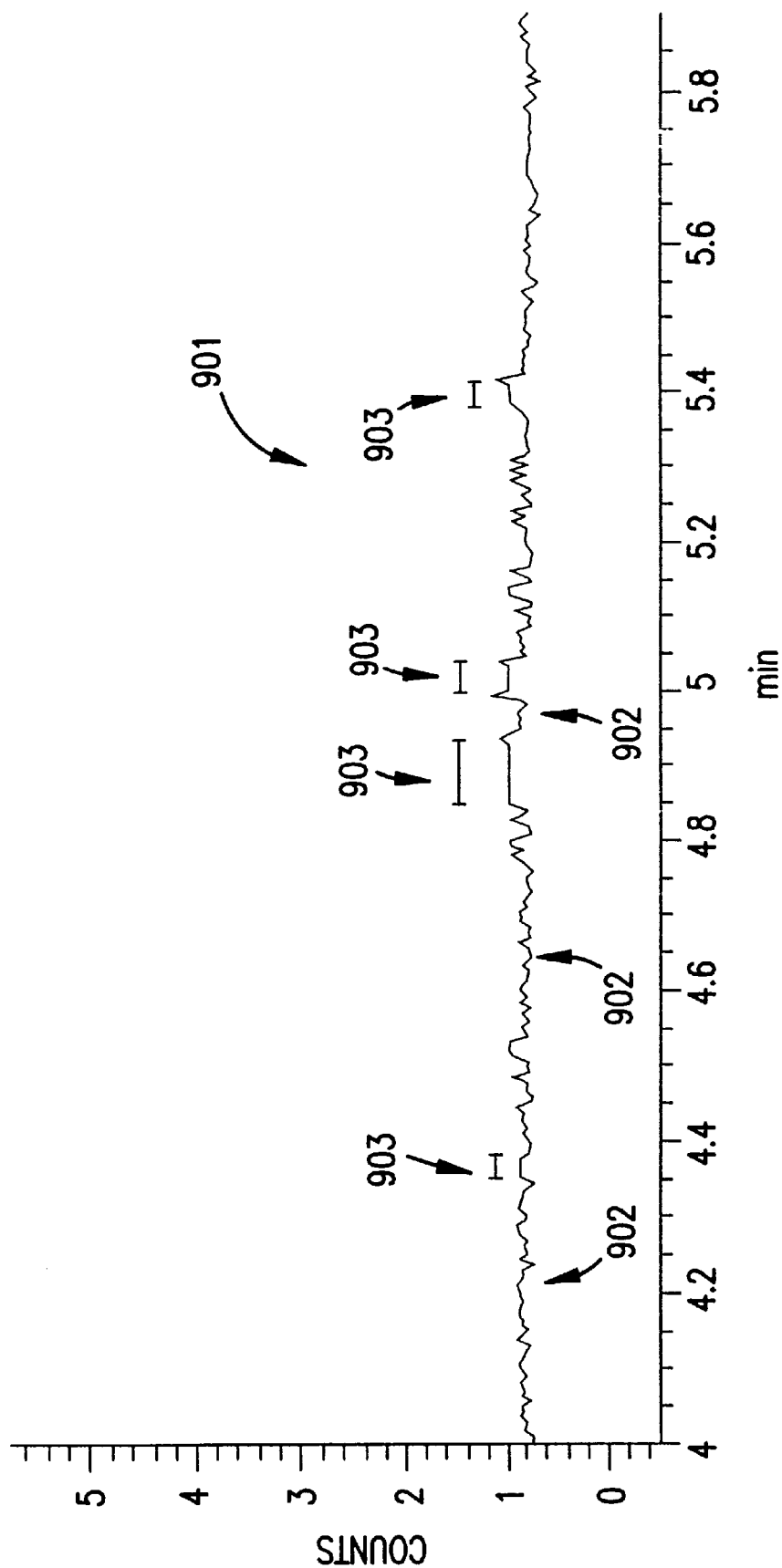
FIG. 9 is an exemplary chromatogram showing the composite baseline (before smoothing) generated by the first iteration of the baseline optimization algorithm operating on the signal of FIG. 1.

The third step 704 is to substitute data from the signal $s(x)$ into the baseline $b(x)$ at those values of x where the baseline-adjusted signal $a(x)$ falls within the noise band defined by the threshold values. After this step has been performed, the baseline 901 in FIG. 9 becomes a composite of signal data 902 at those values of x where the signal approximately consists of background, and previous baseline 903 at those values of x where the signal approximately consists of peaks or negative background disturbances. As will be appreciated by comparing FIG. 9 with FIG. 1, the composite baseline 901 approximates signal 101 data, with peaks 102 and disturbances 106 outside the noise band clipped. Replacing baseline data $b(x)$ with signal data $s(x)$ has the effect of removing from the composite baseline 901 much of the area of the peaks which was included in the baseline 105 following smoothing 701.

Figure 10:
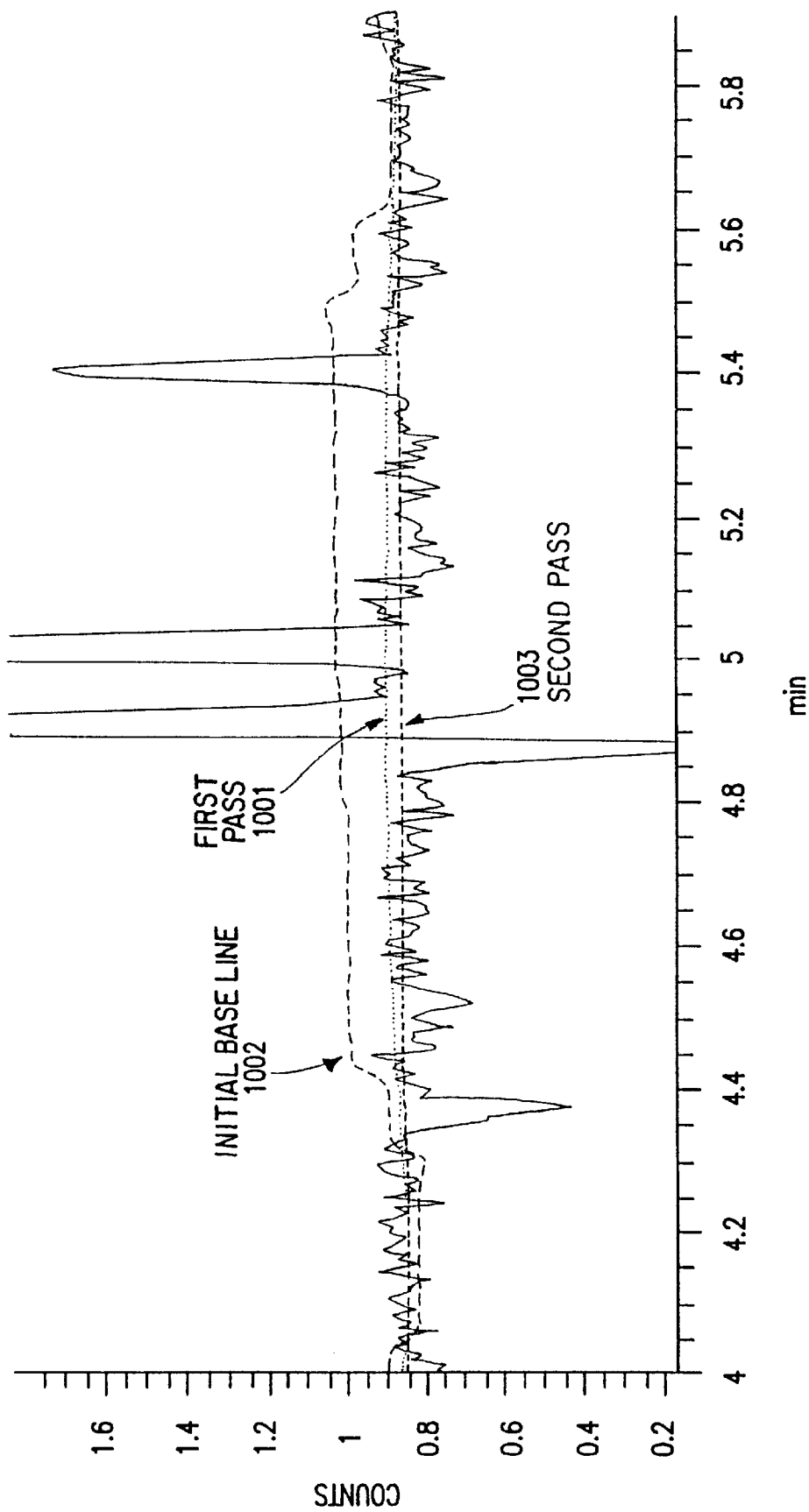
FIG. 10 is an exemplary chromatogram showing, on an expanded scale relative to FIG. 1, the initial approximate baseline, the first pass improved baseline, and the second pass improved baseline generated by the baseline optimization algorithm operating on the signal of FIG. 1.

The fourth step 705 is to smooth the composite baseline 901 to form the improved baseline 1001 which has a reduced error component. Since signal data representing peaks and disturbances outside the threshold values have been removed from the composite baseline 901, they do not distort the first pass improved baseline 1001 in FIG. 10 resulting from the smoothing step 705. It will be appreciated that the first pass improved baseline 1001 is closer to a baseline centered through the noise and drift than the initial baseline 1002, and is closer to a baseline that a chromatographer looking at the chromatogram would draw.

Figure 11:
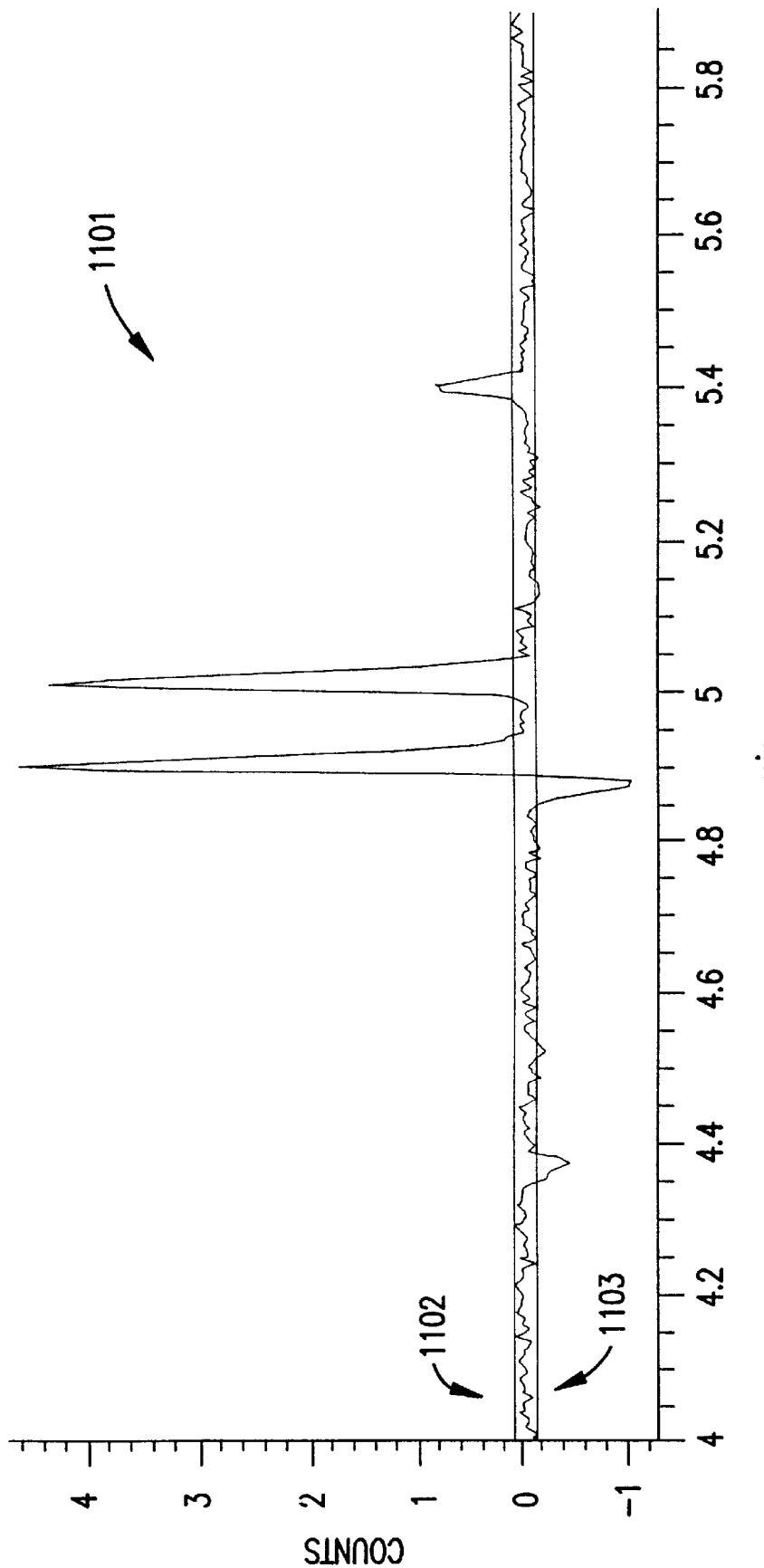
FIG. 11 is an exemplary chromatogram showing the baseline-adjusted signal and the threshold values defining the noise band for the signal of FIG. 1, after the second iteration of the baseline optimization algorithm.

The preceding optimizing steps 702, 703, 705, and 705 may be performed iteratively 706 to further improve the baseline, substituting the improved baseline generated by the previous iteration as the approximate baseline for the next iteration. Because the first pass improved baseline 1001 is more accurate than the initial baseline 1002, the deviations from zero counts in the second pass baseline-adjusted signal 1101 of FIG. 11 are further reduced, allowing second-pass thresholds $t_P$ 1102 and $t_N$ 1103 to be set tighter relative to first-pass thresholds $t_P$ 802 and $t_N$ 803, which in turn results in a more accurate second-pass composite baseline. The second iteration yields the second pass improved baseline 1003 of FIG. 10. For a fairly simple signal with small peaks and disturbances, good results are possible after only one or two iterations, but to handle the more general case the preferred embodiment iterates eight times. Additional iterations of the optimization steps yield further improvement, at the cost of increased processing time.

After the baseline has been optimized, the signal may be integrated via a prior art integration algorithm that uses this optimized baseline to define the time and signal level to use for the starting and ending baseline points for each peak so as to more accurately calculate peak heights and areas.

Signal Filtering Method to Attenuate Drift

Figure 5:
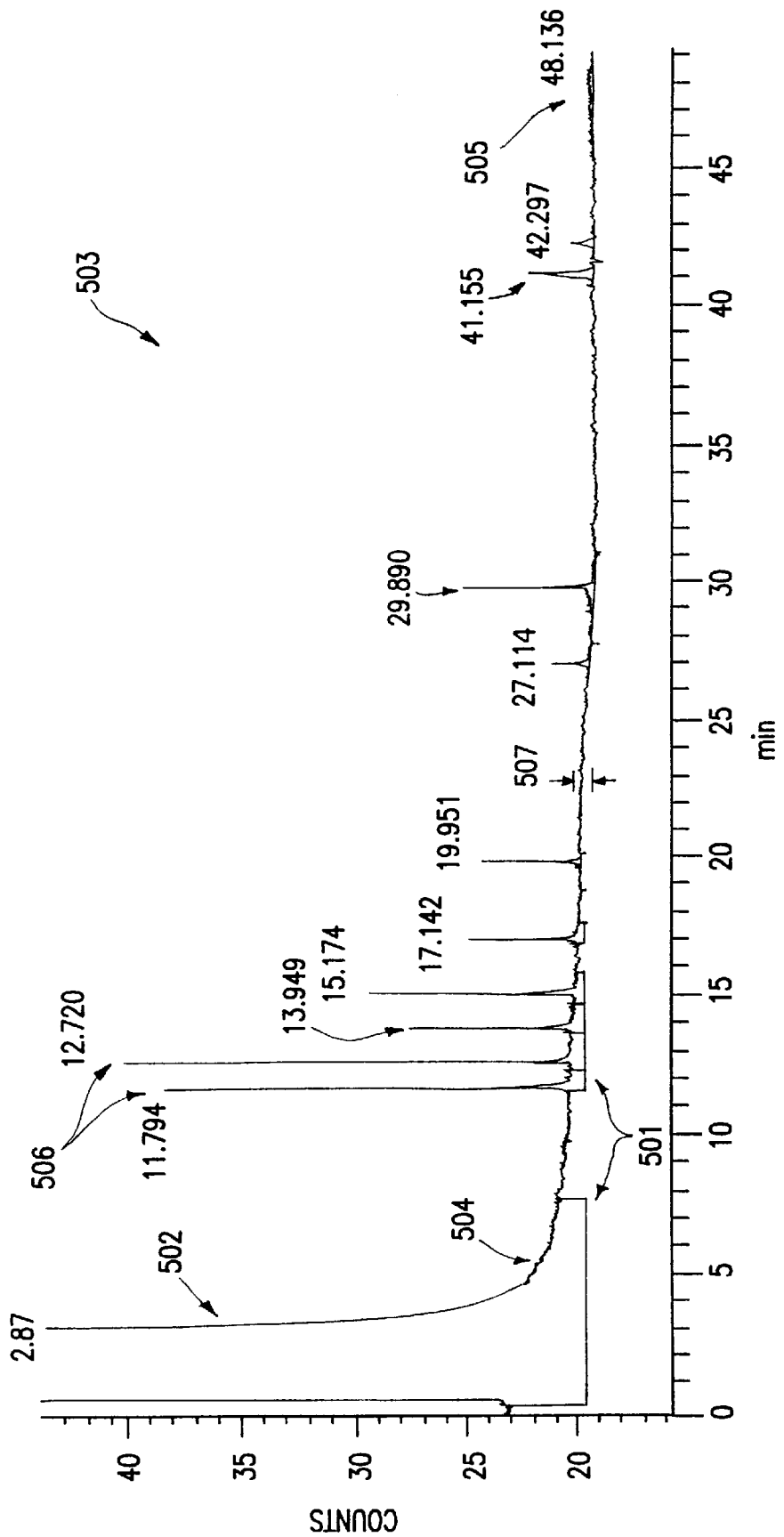
FIG. 5 is an exemplary chromatogram showing a chromatographic signal including peaks, noise, and drift. The chromatogram shows an inaccurate baseline and a false peak resulting from use of a prior art integration method.
Figure 12:
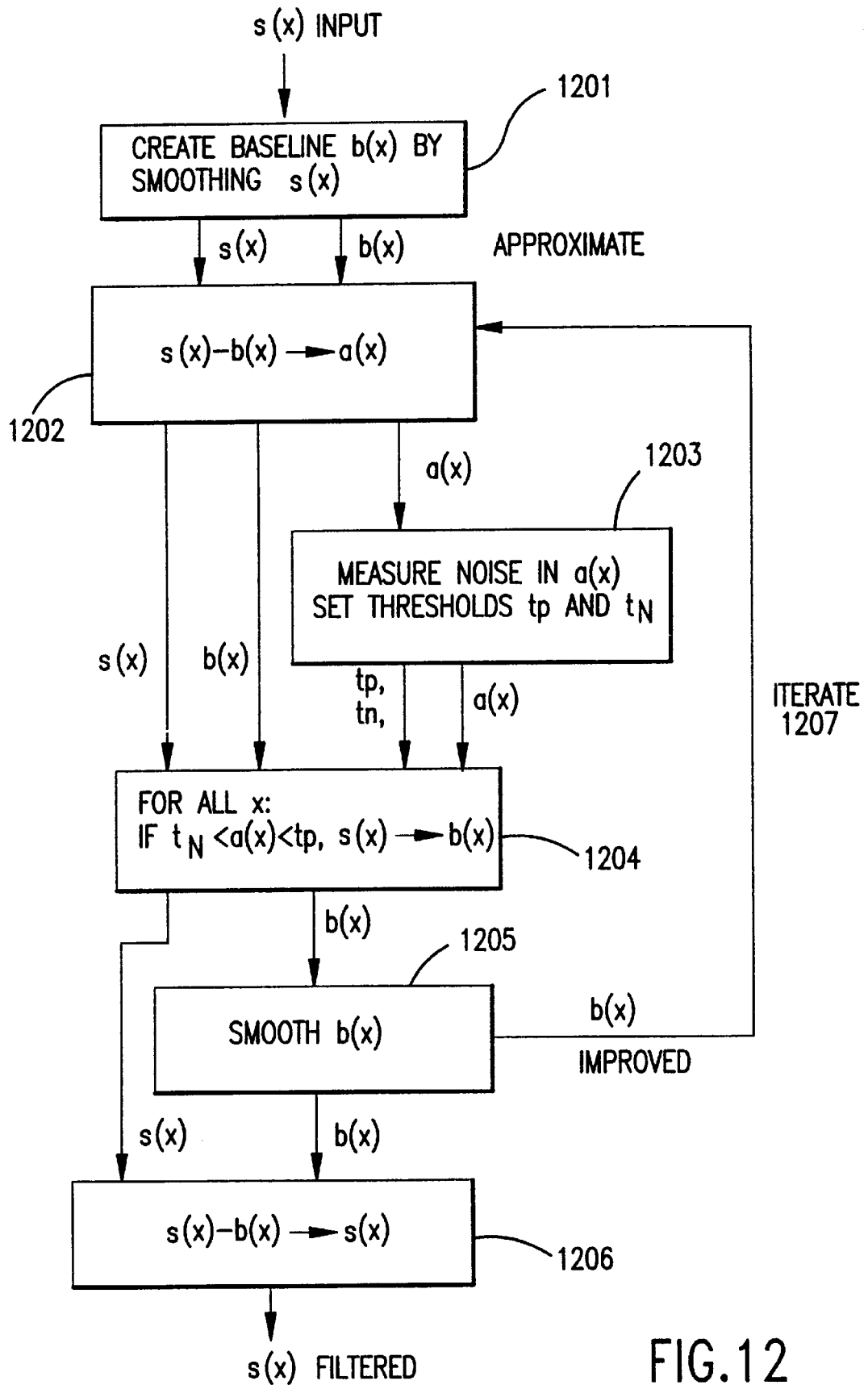
FIG. 12 is a simplified representation of an algorithm for performing signal filtering to attenuate drift in accordance with the present invention.

As illustrated by applying the method of FIG. 12 to the signal data of FIG. 5 by way of example, a preferred second embodiment of the present invention is a novel method of filtering a signal 503 to attenuate background drift 504. The general approach used in the second embodiment is to generate a smoothed composite baseline which tracks the signal drift, and then subtract the baseline from the signal to attenuate the drift. The similarities between this method and the baseline optimization method will be appreciated by those skilled in the art.

This embodiment begins with a step 1201 in which an initial baseline $b(x)$ is generated by smoothing the signal $s(x)$ 503. The smoothing operation generates a baseline that approximately tracks low-frequency phenomena such as background drift but not higher-frequency phenomena such as background noise and peaks.

The second step 1202 is to subtract the baseline $b(x)$ from the signal $s(x)$ 503, the difference forming a baseline-adjusted signal $a(x)$ centered around zero counts. Since the smoothed baseline $b(x)$ tracks drift in the signal but not peaks or noise, it will be appreciated that drift in the baseline-adjusted signal $a(x)$ is attenuated while peaks and noise remain.

The third step 1203 is to calculate the noise in the baseline-adjusted signal $a(x)$ and set positive $(t_P)$ and negative $(t_N)$ threshold values outside the range of, and surrounding, the noise. Signal data at those values of x where the baseline-adjusted signal falls within the noise band defined by the thresholds approximately represent background. Signal data at those values of x where the baseline-adjusted signal falls outside this band approximately represent peaks.

The fourth step 1204 is to substitute data from the signal s(x) into the baseline b(x) at values of x where the baseline-adjusted signal a(x) falls within the noise band defined by the threshold values. Following the performance of this step, the baseline becomes a composite of signal data at those values of x where the signal approximately consists of background, and previous baseline at those values of x where the signal approximately consists of peaks. The composite baseline approximates signal data with any peaks outside the noise band clipped. It will be appreciated that substituting signal data into the baseline makes the composite baseline approximately track the drift and noise in the signal.

The fifth step 1205 is to smooth the composite baseline b(x). The smoothing operation results in a baseline b(x) that still approximately tracks background drift, but the effects of noise get smoothed out and attenuated.

The second, third, fourth, and fifth steps 1202, 1203, 1204, and 1205 above may be performed iteratively 1207 to improve how well the baseline b(x) tracks the background drift, by using the smoothed composite baseline resulting from the previous iteration as the approximate baseline for the next iteration. For a fairly simple signal with small peaks and disturbances, good results are possible after only one or two iterations, but to handle the more general case the preferred embodiment iterates eight times. Additional iterations further attenuate drift, at the cost of increased processing time.

Figure 13:
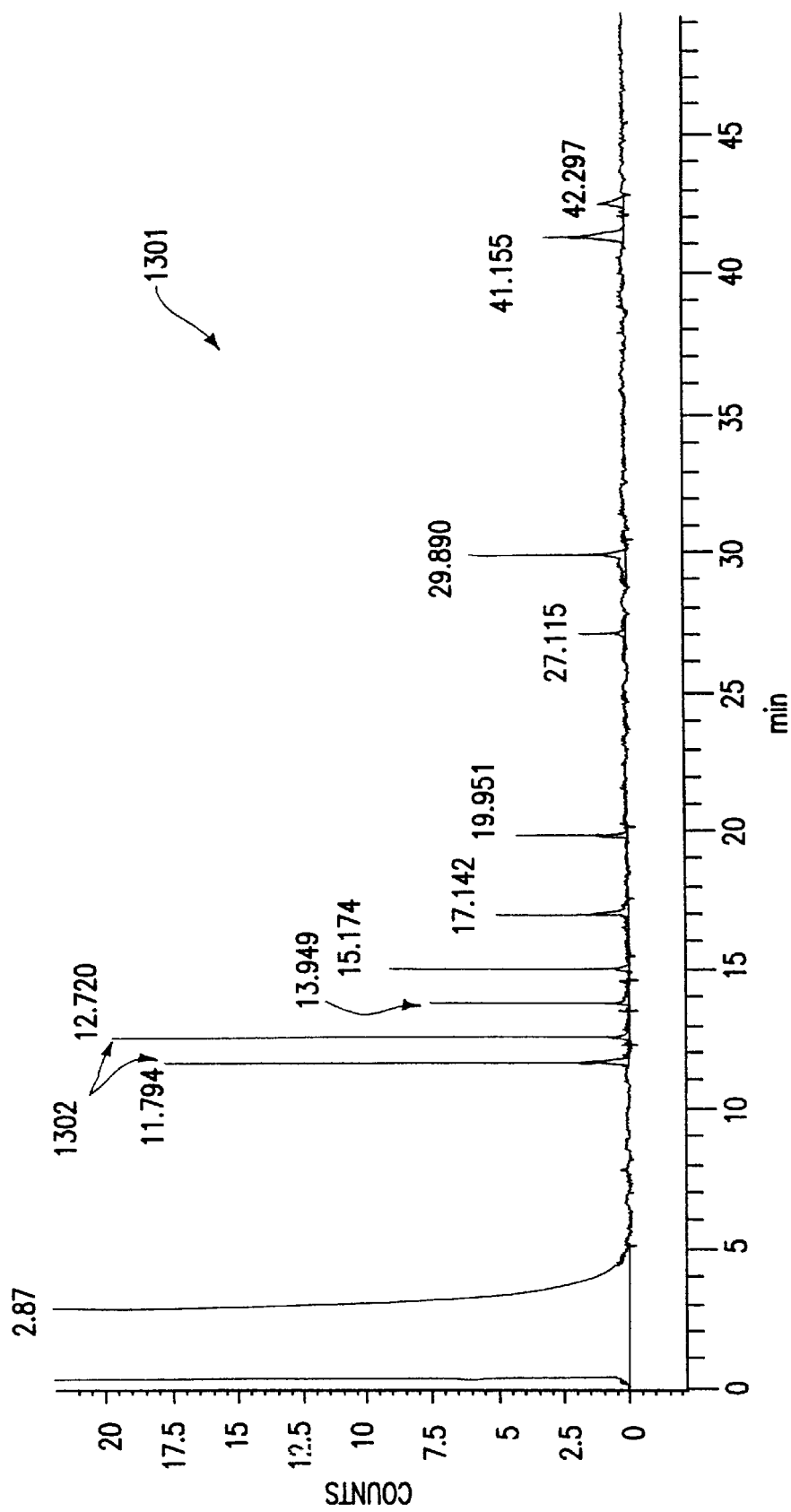
FIG. 13 is an exemplary chromatogram showing the filtered signal resulting from applying the signal filtering method of FIG. 12 to the signal of FIG. 5.

After the final iteration has been performed, the last step 1206 is to subtract the baseline b(x) from the signal s(x) to form the filtered signal 1301 shown in FIG. 13. It will be appreciated that this results in a signal 1301, centered around zero counts, in which background drift has been attenuated but background noise has not. The heights of the peaks 1302 have been adjusted to compensate for drift, as can be seen by comparison to the peaks 506. Peak area is conserved.

The filtered signal may further be displayed as a chromatogram, or it may be integrated via a prior art integration algorithm to calculate peak heights and areas. Since drift has been filtered from the signal, integration is simplified in that a signal level of zero counts may be used for the starting and ending baseline points for all peaks. In addition, false peaks due to drift are eliminated, as can be seen by the absense in FIG. 13 of the false peak 505.

Signal Filtering Method to Attenuate Noise and Drift

Figure 14:
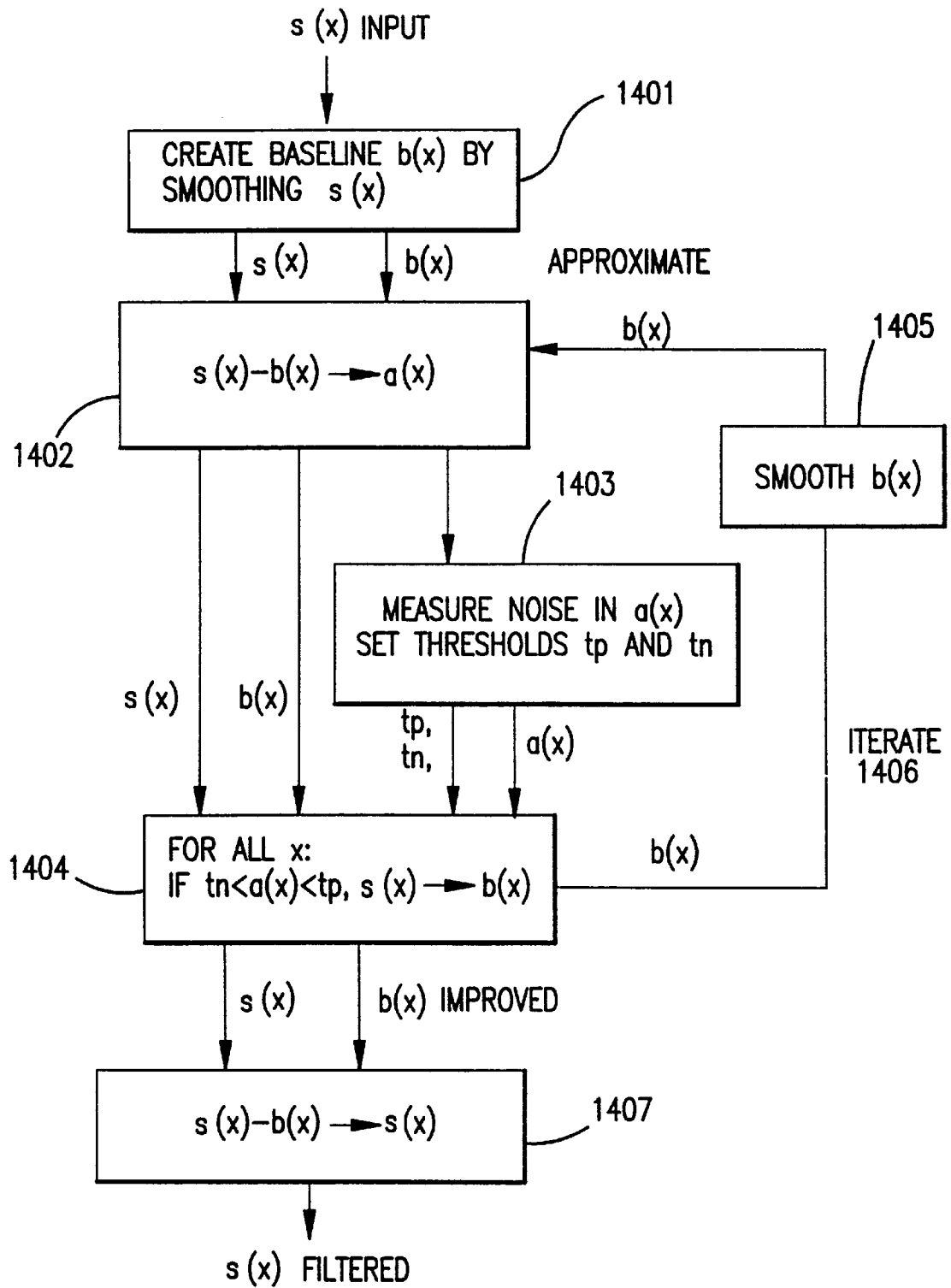
FIG. 14 is a simplified representation of an algorithm for performing signal filtering to attenuate drift and noise in accordance with the present invention.

As illustrated by applying the method of FIG. 14 to the signal data of FIG. 5 by way of example, a preferred third embodiment of the present invention is a novel method of filtering a signal 503 to attenuate both noise 507 and drift 504. The general approach is to generate a smoothed baseline which tracks the signal drift, then create a composite baseline which tracks the signal noise, and finally subtract the composite baseline from the signal to attenuate the drift and noise. The similarities between this method and the signal filtering method to attenuate drift described previously will be appreciated by those skilled in the art.

This embodiment begins with a step 1401 in which an initial approximate baseline b(x) is generated by smoothing the signal s(x) 503. The smoothing operation generates a baseline that tracks low-frequency phenomena such as drift but not higher-frequency phenomena such as noise and peaks.

The second step 1402 is to subtract the baseline b(x) from the signal s(x) 503, the difference forming a baseline-adjusted signal a(x) centered around zero counts. Since the smoothed baseline b(x) tracks drift in the signal but not peaks or noise, it will be appreciated that drift in the baseline-adjusted signal a(x) is attenuated while peaks and noise remain.

The third step 1403 is to calculate the noise in the baseline-adjusted signal a(x) and set positive ($t_P$) and negative ($t_N$) threshold values outside the range of, and surrounding, the noise. Signal data at those values of x where the baseline-adjusted signal falls within the noise band defined by the thresholds approximately represent background. Signal data at those values of x where the baseline-adjusted signal falls outside this band approximately represent peaks.

The fourth step 1404 is to substitute data from the signal s(x) into the baseline b(x) at values of x where the baseline-adjusted signal a(x) falls within the noise band defined by the threshold values. Following the performance of this step, the baseline becomes a composite of signal data at those values of x where the signal approximately consists of background, and previous baseline at those values of x where the signal approximately consists of peaks. The composite baseline approximates signal data with any peaks outside the noise band clipped. It will be appreciated that substituting signal data into the baseline makes the composite baseline approximately track the drift and noise in the signal.

Figure 15:
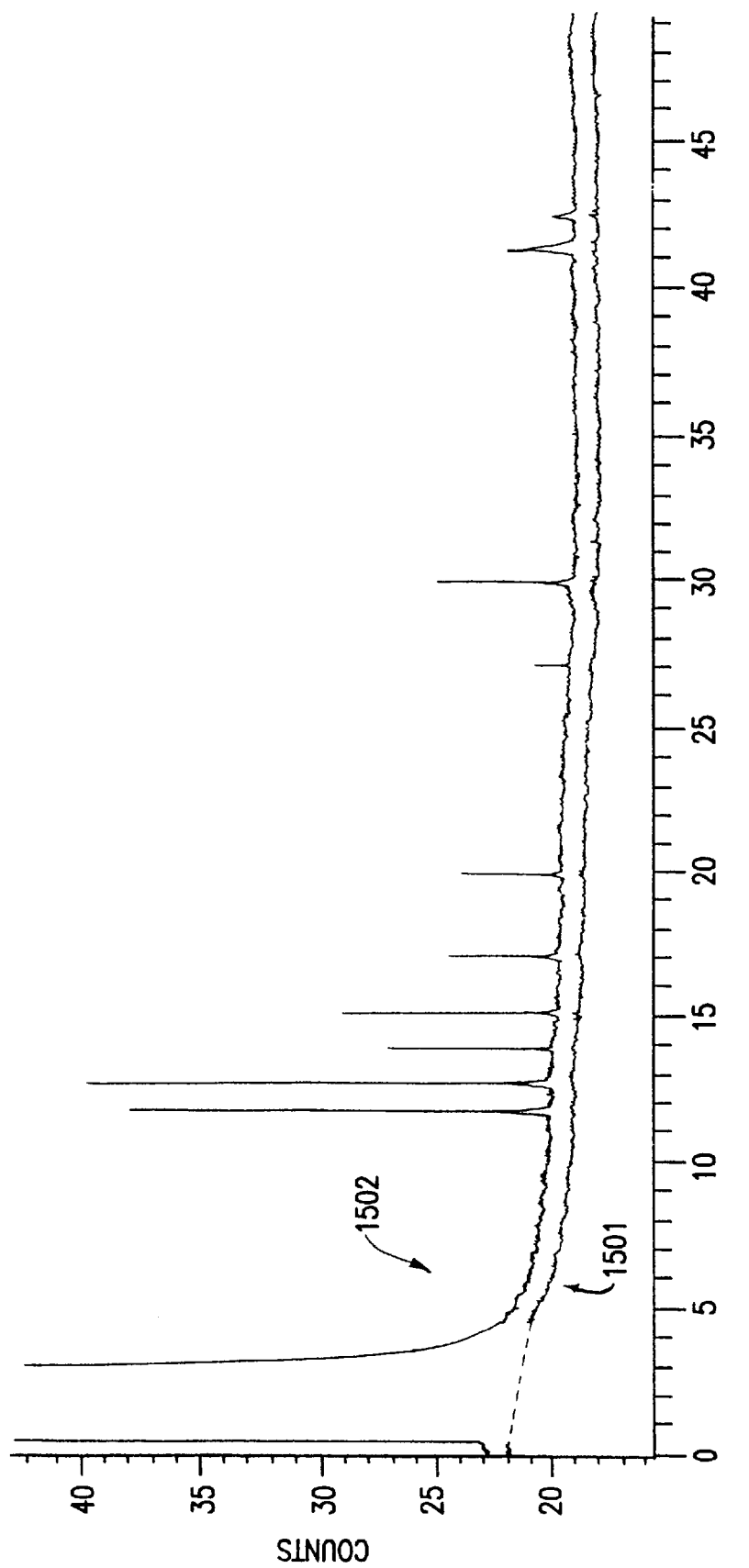
FIG. 15 is an exemplary chromatogram showing the composite baseline (offset slightly downward for viewability) generated by applying the signal filtering method of FIG. 14 to the signal of FIG. 5.

The second, third, and fourth steps above may be performed iteratively 1406 to further improve how well the composite baseline tracks the background drift and noise. If the method is performed iteratively, the composite baseline b(x) generated by the fourth step 1404 of the prior iteration will be smoothed 1405 and then will replace the approximate baseline used for performing the subtraction step 1402 of the next iteration. For a fairly simple signal with small peaks and disturbances, good results are possible after only one or two iterations, but to handle the more general case the preferred embodiment iterates eight times. Additional iterations further attenuate drift and noise, at the cost of increased processing time. FIG. 15 shows the composite baseline 1501 produced by the final iteration, overlaid with the signal 1502 (for purposes of clarity, the baseline is illustrated offset slightly downward). It will be appreciated that the baseline closely tracks the signal everywhere but where peaks are present.

Figure 16:
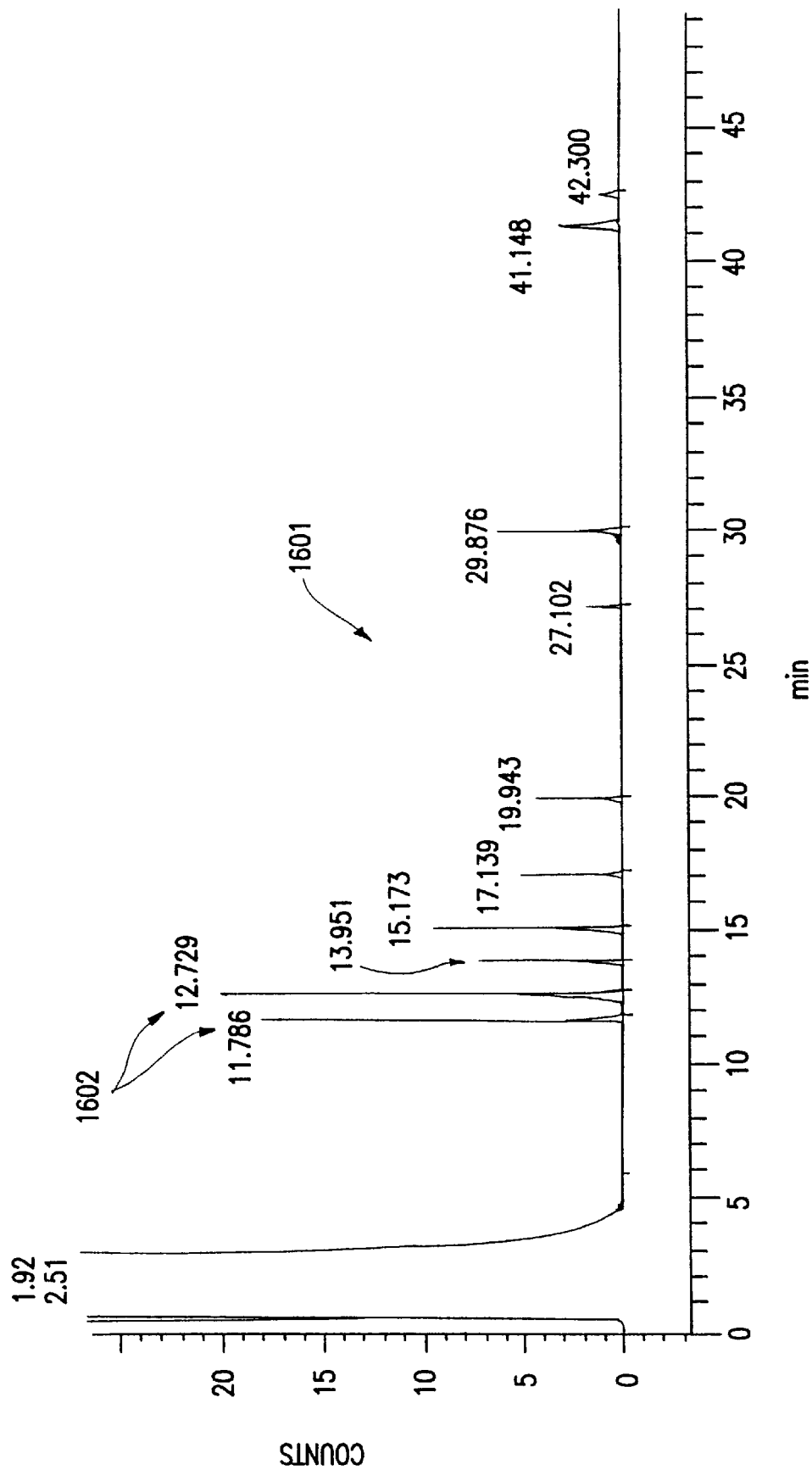
FIG. 16 is an exemplary chromatogram showing the filtered signal resulting from applying the signal filtering method of FIG. 14 to the signal of FIG. 5.

Once iteration has been completed and the final composite baseline b(x) has been obtained, the composite baseline is subtracted 1407 from the signal s(x). As shown in FIG. 16, the background drift and noise are attenuated; in fact, after sufficient iterations the resulting signal s(x) 1601 will be zero counts everywhere except where peaks 1602 exist. The height of the peaks 1602 above the baseline is unchanged, as can be seen by comparison to the peaks 506, and peak area is conserved. In addition, false peaks due to drift are eliminated, as can be seen by the absence in FIG. 16 of the false peak 505.

The drift-adjusted signal may further be displayed as a simple chromatogram, or it may be integrated via a prior art integration algorithm to calculate peak heights and areas. Since drift and noise have been filtered from the signal, integration is simplified. A signal level of zero counts is used for the starting and ending baseline points of all peaks, and a simple peak detector will suffice since any positive deviation from zero counts indicates a peak. In addition, false peaks due to drift are eliminated, as can be seen by the absence in FIG. 16 of the false peak 505.

Another application of this filtering method is in simulated distillation, which does not involve integration. In simulated distillation the signal is divided up into small segments called area slices. Each area slice corresponds to a certain boiling range of a hydrocarbon mixture. Which peaks make up the area within a slice is not important, since all peaks in the slice have approximately the same boiling point; rather, it is the total area under the peaks of each slice that are measured. Significant errors result from simulated distillation when noise and drift are significant relative to the signal. However, by using this filtering method to remove drift and noise from the signal prior to performing simulated distillation, the area slices will only contain the area of the peaks. This technique is only applicable where there are discrete peaks, as in lower-boiling mixtures. Higher boiling ranges tend to produce "humps" of highly merged peaks and the filtering method will treat the humps as drift and subtract out much of their area.

Signal Filtering to Attenuate Noise

Figure 17:
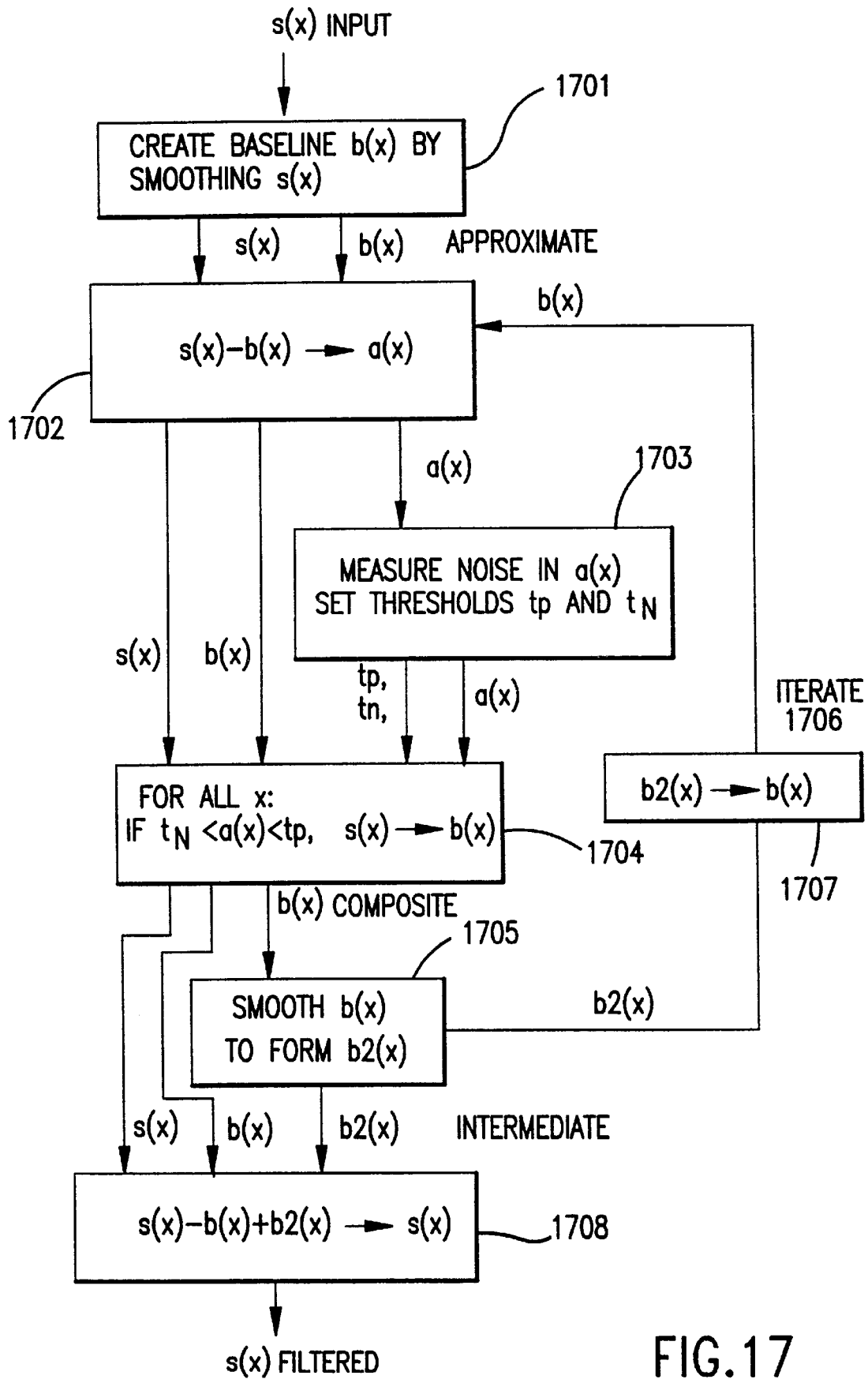
FIG. 17 is a simplified representation of an algorithm for performing signal filtering to attenuate noise in accordance with the present invention.

As illustrated by applying the method of FIG. 17 to the signal data of FIG. 5 by way of example, a preferred fourth embodiment of the present invention is a novel method of filtering a signal 503 to attenuate noise 507. The general approach is to form a composite baseline which tracks noise and drift, then smooth the composite baseline to form an intermediate baseline which tracks only drift, subtract the composite baseline from the signal to attenuate both noise and drift, and finally add the intermediate baseline back in to reconstitute the drift. Those skilled in the art will appreciate that this method combines elements of the two signal filtering methods described above.

This embodiment begins with a step 1701 in which an initial baseline b(x) is generated by smoothing the signal s(x) 503. The smoothing operation generates a baseline that tracks low-frequency phenomena such as drift but not higher-frequency phenomena such as noise and peaks.

The second step 1702 is to subtract the baseline b(x) from the signal s(x), the difference forming a baseline-adjusted signal a(x) centered around zero counts. Since the smoothed baseline b(x) tracks drift in the signal but not peaks or noise, it will be appreciated that the drift in the baseline-adjusted signal a(x) is attenuated while peaks and noise remain.

The third step 1703 is to calculate the noise in the baseline-adjusted signal a(x) and set positive ($t_P$) and negative ($t_N$) threshold values outside the range of, and surrounding, the noise. Signal data at those values of x where the baseline-adjusted signal falls within the noise band defined by the thresholds approximately represent background. Signal data at those values of x where the baseline-adjusted signal falls outside this band approximately represent peaks.

The fourth step 1704 is to substitute data from the signal s(x) into the baseline b(x) at values of x where the baseline-adjusted signal a(x) falls within the noise band defined by the threshold values. Following the performance of this step, the baseline becomes a composite of signal data at those values of x where the signal approximately consists of background, and previous baseline at those values of x where the signal approximately consists of peaks. The composite baseline approximates signal data with any peaks outside the noise band clipped. It will be appreciated that substituting signal data into the baseline makes the composite baseline approximately track the background drift and noise in the signal.

The fifth step 1705 is to smooth the composite baseline b(x) to form an intermediate baseline b2(x) that still approximately tracks background drift, but no longer tracks background noise due to effects of the smoothing operation.

The second, third, fourth, and fifth steps above may be performed iteratively 1706 to further improve how well the composite baseline b(x) and the intermediate baseline b2(x) track the background. If the method is performed iteratively, the intermediate baseline b2(x) generated by the fifth step 1705 of the prior iteration will replace the baseline b(x) 1707 for the subtraction step 1702 of the next iteration. For a fairly simple signal with small peaks and disturbances, good results are possible after only one or two iterations, but to handle the more general case the preferred embodiment iterates eight times. Additional iterations further attenuate noise, at the cost of increased processing time.

Figure 18:
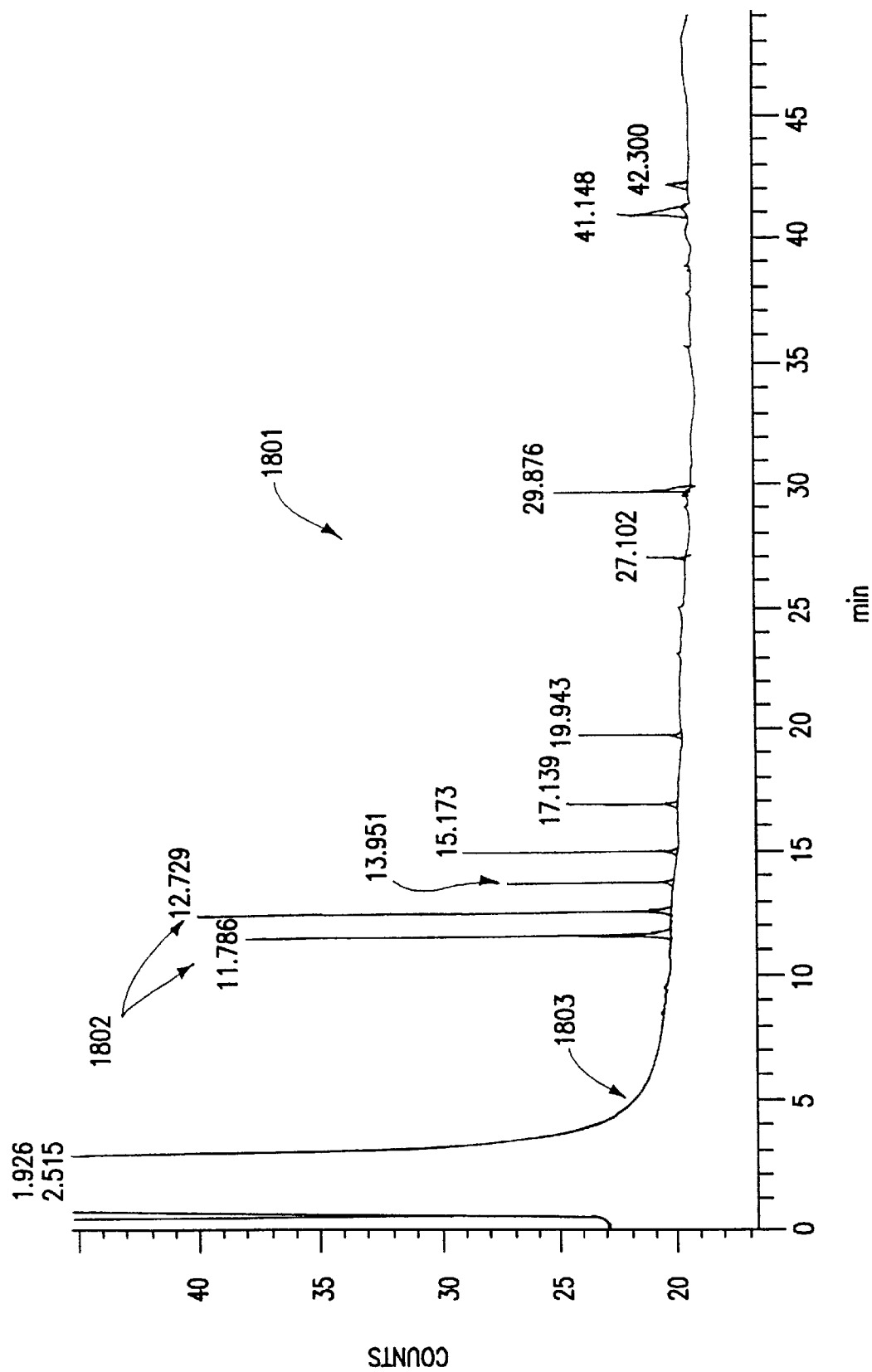
FIG. 18 is an exemplary chromatogram showing the filtered signal resulting from applying the signal filtering method of FIG. 17 to the signal of FIG. 5.

Once iteration has been completed and the final composite baseline b(x) and intermediate baseline b2(x) have been obtained, the composite baseline is subtracted 1708 from the signal s(x) to attenuate the background drift and noise, and the intermediate baseline b2(x) is added 1708 to the signal s(x) to add the background drift back in. As shown in FIG. 18, the background noise is attenuated while the drift 1803 is generally unaffected. As a result, the amplitude of peaks 1802 is substantially the same as the peaks 506 in the original signal 503. It will be appreciated that because of the addition of the background drift, the resulting signal s(x) 1801 will not be centered around zero counts, but around the level of the original background drift 1803.

The drift-adjusted signal may further be displayed as a chromatogram which shows the drift in the signal without the masking effects of noise. The signal may also be integrated via a prior art integration algorithm to calculate peak heights and areas.

Conclusion

From the foregoing it will be apparent that the invention provides novel and advantageous methods of optimizing the baseline of a signal to properly account for the effects of noise and drift, and of filtering drift, noise, or both from a signal prior to performing subsequent processing operations. An accurate baseline ensures proper peak recognition and produces accurate integration results for peak height and peak area. Prefiltering the signal to remove drift and noise provides a visually cleaner display, allows integration to be performed by simpler and faster algorithms, and allows accurate simulated distillation to be performed.

Although several specific embodiments of the invention have been described and illustrated in the area of gas chromatography, the invention is not to be limited to the specific forms, methods, or arrangements of parts so described and illustrated. For example, the embodiments of the invention described herein may operate upon signals which are generated by other electronic instruments such as spectrum analyzers and seismographs. The invention is defined by the claims.

What is claimed is:

1. A method for improving the accuracy of an approximate baseline for an input signal, the approximate baseline having a first error component, and the input signal having a background level, comprising the method steps of:

acquiring the input signal;

subtracting the approximate baseline from the input signal to form a baseline-adjusted signal having baseline-adjusted noise;

calculating first and second threshold values surrounding the range of the baseline-adjusted noise and defining a noise band between the first and second threshold values;

substituting the input signal for the approximate baseline wherever the baseline-adjusted signal falls within the noise band to form a composite baseline; and smoothing the composite baseline to form an improved baseline having a second error component smaller than the first error component.

2. The method for improving the accuracy of an approximate baseline for an input signal as claimed in claim 1, further comprising the method step of replacing the approximate baseline with the improved baseline, wherein the method steps are performed iteratively such that the second error component is further attenuated with each iteration.

3. The method for improving the accuracy of an approximate baseline for an input signal as claimed in claim 1, wherein the input signal is chromatographic data.

4. The method for improving the accuracy of an approximate baseline for an input signal as claimed in claim 1, further comprising the method step of integrating the input signal using the improved baseline.

5. The method for improving the accuracy of an approximate baseline for an input signal as claimed in claim 1 wherein x is a variable and the approximate baseline further comprises a data structure b(x), the input signal further comprises a data structure s(x) having a value, the baseline-adjusted signal further comprises a data structure a(x), and wherein the method step of substituting the input signal for the approximate baseline further comprises substituting the value of s(x) into b(x) at all values of x where a(x) falls within the noise band.

6. A method for filtering an input signal having a background level, comprising the method steps of:

acquiring the input signal;

smoothing the input signal to form an approximate baseline;

subtracting the approximate baseline from the input signal to form a baseline-adjusted signal having baseline-adjusted noise;

calculating first and second threshold values surrounding the range of the baseline-adjusted noise and defining a noise band between the first and second threshold values; and substituting the input signal for the approximate baseline wherever the baseline-adjusted signal falls within the noise band to form a composite baseline.

7. The method for filtering an input signal having a background level as claimed in claim 6, wherein the background level includes a first drift component, further comprising the method steps of:

smoothing the composite baseline to form an improved baseline; and subtracting the improved baseline from the input signal to form a filtered signal having a second drift component attenuated relative to the first drift component.

8. The method for filtering an input signal having a background level as claimed in claim 7, further comprising the method step of replacing the approximate baseline with the improved baseline, and wherein the method steps of subtracting the approximate baseline, calculating first and second threshold values, substituting the input signal for the approximate baseline, smoothing the composite baseline, and replacing the approximate baseline are performed iteratively such that the second drift component is further attenuated with each iteration.

9. The method for filtering an input signal having a background level as claimed in claim 6, wherein the background level includes a first drift component and a first noise component, further comprising the method step of subtracting the composite baseline from the input signal to form a filtered signal having a second drift component attenuated relative to the first drift component, and a second noise component attenuated relative to the first noise component.

10. The method for filtering an input signal having a background level as claimed in claim 9, further comprising the method steps of:

smoothing the composite baseline to form an improved baseline, and replacing the approximate baseline with the improved baseline;

wherein the method steps of subtracting the approximate baseline, calculating first and second threshold values, substituting the input signal for the approximate baseline, smoothing the composite baseline, and replacing the approximate baseline are performed iteratively such that the second drift component and second noise component are further attenuated with each iteration.

11. The method for filtering an input signal having a background level as claimed in claim 9, wherein the input signal is chromatographic data, further comprising the method step of performing simulated distillation calculations on the filtered signal.

12. The method for filtering an input signal having a background level as claimed in claim 6, wherein the background level includes a first noise component, further comprising the method steps of:

smoothing the composite baseline to form an intermediate baseline; and forming a filtered signal having a second noise component attenuated relative to the first noise component by subtracting the composite baseline from, and adding the intermediate baseline to, the input signal.

13. The method for filtering an input signal having a background level as claimed in claim 12, further comprising the method step of replacing the approximate baseline with the intermediate baseline, and wherein the method steps of subtracting the approximate baseline, calculating first and second threshold values, substituting the input signal for the approximate baseline, smoothing the composite baseline, and replacing the approximate baseline are performed iteratively such that the second noise component is further attenuated with each iteration.

14. A program storage medium readable by a computer, tangibly embodying a program of instructions executable by the computer for improving the accuracy of an approximate baseline for an input signal, the approximate baseline having a first error component, and the input signal having a background level, the program storage medium comprising:

a first segment of the instructions configured to subtract the approximate baseline from the input signal to form a baseline-adjusted signal having baseline-adjusted noise;

a second segment of the instructions configured to calculate first and second threshold values surrounding the range of the baseline-adjusted noise and define a noise band between the first and second threshold values;

a third segment of the instructions configured to substitute the input signal for the approximate baseline wherever the baseline-adjusted signal falls within the noise band to form a composite baseline; and a fourth segment of the instructions configured to smooth the composite baseline to form an improved baseline having a second error component smaller than the first error component.

15. A program storage medium readable by a computer, tangibly embodying a program of instructions executable by the computer for filtering an input signal having a background level, the program storage medium comprising:

a first segment of the instructions configured to smooth the input signal to form an approximate baseline;

a second segment of the instructions configured to subtract the approximate baseline from the input signal to form a baseline-adjusted signal having baseline-adjusted noise;

a third segment of the instructions configured to calculate first and second threshold values surrounding the range of the baseline-adjusted noise and define a noise band between the first and second threshold values; and a fourth segment of the instructions configured to substitute the input signal for the approximate baseline wherever the baseline-adjusted signal falls within the noise band to form a composite baseline.

16. The program storage medium readable by a computer as claimed in claim 15, wherein the background level includes a first drift component, further comprising:

a fifth segment of the instructions configured to smooth the composite baseline to form an improved baseline; and a sixth segment of the instructions configured to subtract the improved baseline from the input signal to form a filtered signal having a second drift component attenuated relative to the first drift component.

17. The program storage medium readable by a computer as claimed in claim 15, wherein the background level includes a first drift component and a first noise component, further comprising a fifth segment of the instructions configured to subtract the composite baseline from the input signal to form a filtered signal having a second drift component attenuated relative to the first drift component, and a second noise component attenuated relative to the first noise component.

18. The program storage medium readable by a computer as claimed in claim 15, wherein the background level includes a first noise component, further comprising:

a fifth segment of the instructions configured to smooth the composite baseline to form an intermediate baseline; and a sixth segment of the instructions configured to form a filtered signal having a second noise component attenuated relative to the first noise component by subtracting the composite baseline from, and adding the intermediate baseline to, the input signal.

19. A data analysis system, comprising:

an input for receiving an input signal having at least one peak and further having a background level including background noise; and a processor in communication with the input which
subtracts an approximate baseline from the input signal to form a baseline-adjusted signal having baseline-adjusted noise,
calculates first and second threshold values surrounding the range of the baseline-adjusted noise thus defining a noise band between the first and second threshold values, and
substitutes the input signal for the approximate baseline wherever the baseline-adjusted signal falls within the noise band to form a composite baseline.

20. The data analysis system of claim 19, further comprising a chromatograph connected to the input, the chromatograph adapted for receiving a chemical sample having at least one component, the chromatograph further having a column for separating the chemical sample into the at least one component and a detector responsive to the at least one component for generating the input signal.

21. The data analysis system of claim 19, further comprising an output device, wherein the processor further smoothes the composite baseline to form an improved baseline, integrates the input signal using the improved baseline, and transmits the integrated input signal to the output device.

* * * * *